(12) United States Patent
Davis et al.

(10) Patent No.: US 8,050,740 B2
(45) Date of Patent: Nov. 1, 2011

(54) MICROWAVE-BASED EXAMINATION USING HYPOTHESIS TESTING

(75) Inventors: Shakti K. Davis, Madison, WI (US); Susan C. Hagness, Madison, WI (US); Barry D. Van Veen, McFarland, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2067 days.

(21) Appl. No.: 10/942,115

(22) Filed: Sep. 15, 2004

(65) Prior Publication Data
US 2006/0058606 A1   Mar. 16, 2006

(51) Int. Cl.
*A61B 5/00* (2006.01)

(52) U.S. Cl. ........ 600/430; 600/407; 607/101; 324/637; 324/638

(58) Field of Classification Search .......... 600/430, 600/407, 408; 607/154–156, 101; 324/637–648
See application file for complete search history.

(56) References Cited

U.S. PATENT DOCUMENTS

| | | | |
|---|---|---|---|
| 5,016,018 A | | 5/1991 | Chang et al. |
| 5,363,050 A | | 11/1994 | Guo et al. |
| 5,570,691 A | | 11/1996 | Wright et al. |
| 5,704,355 A | | 1/1998 | Bridges |
| 5,706,013 A | * | 1/1998 | Melvin et al. ........ 342/159 |
| 5,807,257 A | * | 9/1998 | Bridges ........ 600/430 |
| 5,829,437 A | * | 11/1998 | Bridges ........ 600/430 |
| 5,942,899 A | | 8/1999 | Shrekenhamer et al. |
| 6,005,916 A | | 12/1999 | Johnson et al. |
| 6,061,589 A | * | 5/2000 | Bridges et al. ........ 600/430 |
| 6,091,361 A | * | 7/2000 | Davis et al. ........ 342/378 |
| 6,161,034 A | | 12/2000 | Burbank et al. |
| 6,421,550 B1 | * | 7/2002 | Bridges et al. ........ 600/407 |
| 6,448,788 B1 | | 9/2002 | Meaney et al. |
| 7,061,970 B2 | * | 6/2006 | Reed et al. ........ 375/148 |
| 2002/0061280 A1 | | 5/2002 | Mattrey |
| 2002/0163480 A1 | | 11/2002 | Eiges |

(Continued)

OTHER PUBLICATIONS

Shakti K. Davis, et al., "Microwave-Based Detection of Breast Cancer Using the Generalized Likelihood Ratio Test," Proceedings of the IEEE Workshop on Statistical Signal Processing, St. Louis, MO, Sep.-Oct. 2003, pp. 617-620.

(Continued)

*Primary Examiner* — Brian Casler
*Assistant Examiner* — Amanda Lauritzen
(74) *Attorney, Agent, or Firm* — Bell & Manning, LLC

(57) ABSTRACT

Microwave examination of individuals is carried out by transmitting microwave signals from multiple antenna locations into an individual and receiving the backscattered microwave signals at multiple antenna locations to provide received signals from the antennas. The received signals are processed to remove the skin interface reflection component of the signal and the corrected signal data are provided to a hypothesis testing process. In hypothesis testing for detecting tumors, image data are formed from the test statistic used to perform a binary hypothesis test at each voxel. The null hypothesis asserts that no tumor is present at a candidate voxel location. The voxel threshold is determined by specifying a false discovery rate to control the expected proportion of false positives in the image. When the test statistic value associated with a voxel is greater than the threshold, the null hypothesis is rejected and the test statistic is assigned to the voxel. For voxels where the test statistic falls below the threshold, the null hypothesis is accepted and the voxel value is set to zero. The resulting image indicates the locations or other characteristics of detected tumors.

41 Claims, 17 Drawing Sheets

U.S. PATENT DOCUMENTS

| | | | |
|---|---|---|---|
| 2002/0197209 A1 | 12/2002 | Mattrey | |
| 2003/0088180 A1* | 5/2003 | Van Veen et al. | 600/430 |
| 2004/0167399 A1 | 8/2004 | Li | |
| 2005/0251018 A1 | 11/2005 | Gleman | |
| 2005/0259621 A1* | 11/2005 | Lee | 370/335 |
| 2006/0058606 A1 | 3/2006 | Davis et al. | |
| 2006/0183995 A1* | 8/2006 | Bond et al. | 600/407 |
| 2007/0282200 A1* | 12/2007 | Johnson et al. | 600/437 |

OTHER PUBLICATIONS

International Search Report dated Dec. 15, 2006 for PCT/US2006/004533.

No-Weon Kang, et al., "A New 2-D Image Reconstruction Algorithm Based on FDTD and Design Sensitivity Analysis," IEEE Transactions on Microwave Theory and Techniques, vol. 50, No. 12, Dec. 2002, pp. 2734-2740.

* cited by examiner

MICROWAVE-BASED EXAMINATION USING HYPOTHESIS TESTING

REFERENCE TO GOVERNMENT RIGHTS

This invention was made with United States government support awarded by the following agencies: NIH CA092188. The United States government has certain rights in this invention.

FIELD OF THE INVENTION

The present invention pertains generally to the field of medical examination and imaging and particularly to microwave examination of tissue for the detection and location of tumors.

BACKGROUND OF THE INVENTION

Various imaging techniques have been employed for detecting and locating cancerous tumors in body tissue. X-ray and ultrasound imaging techniques are commonly utilized in screening for breast cancer. X-ray mammography is the most effective current method for detecting early stage breast cancer. However, X-ray mammography suffers from relatively high false positive and false negative rates, requires painful breast compression, and exposes the patient to low levels of ionizing radiation.

Microwave based imaging methods have been proposed for use in imaging of breast tissue and other body tissues as an alternative to current ultrasound and X-ray imaging techniques. Microwave imaging does not require breast compression, does not expose the patient to ionizing radiation, and can be applied at low power levels. Microwave-based imaging exploits the contrast in dielectric properties between normal and malignant tissue. With microwave tomography, the dielectric-properties profile of an object being imaged is recovered from measurement of the transmission of microwave energy through the object. This approach requires the solution of an ill-conditioned nonlinear inverse-scattering problem which requires elaborate image reconstruction algorithms. An alternative microwave imaging approach is based on microwave radar methods that use the measured scattered signal to infer the locations of significant sources of scattering in the object being imaged, and are simpler to implement and more robust. Microwave radar methods require the focusing of the received signal in both space and time to discriminate against clutter and to obtain acceptable resolution. This may be accomplished with an antenna array and ultra-wideband microwave probe signals. For a discussion of this approach, see, S. C. Hagness, et al., "Two-Dimensional FDTD Analysis of a Pulsed Microwave Confocal System for Breast Cancer Detection: Fixed Focus and Antenna-Array Sensors," IEEE Trans. Biomed. Eng., Vol. 45, Dec., 1998, pp. 1470-1479; S. C. Hagness, et al., "Three-Dimensional FDTD Analysis of a Pulsed Microwave Confocal System for Breast Cancer Detection: Design of an Antenna-Array Element," IEEE Trans. Antennas and Propagation, Vol. 47, May, 1999, pp. 783-791; S. C. Hagness, et al., "Dielectric Characterization of Human Breast Tissue and Breast Cancer Detection Algorithms for Confocal Microwave Imaging," Proc. of the $2^{nd}$ World Congress on Microwave and Radio Frequency Processing, Orlando, Fla., April, 2000; X. Li and S. C. Hagness, "A Confocal Microwave Imaging Algorithm for Breast Cancer Detection," IEEE Microwave and Wireless Components Letters, Vol.11, No. 3, March, 2001, pp.130-132; and E. Fear, et al, "Confocal microwave imaging for breast cancer detection: Localization of tumors in three dimensions," IEEE Transactions on Biomedical Engineering, vol. 49, no. 8, August 2002, pp. 812-822.

This approach has been extended using space-time beamforming. E. J. Bond, et al., "Microwave Imaging Via Space-Time Beamforming for Early Detection of Breast Cancer," IEEE Trans. Antennas and Propagation, Vol. 51, No. 8, August 2003, pp.1690-1705; S. K. Davis, et al, "Microwave imaging via space-time beamforming for early detection of breast cancer: Beamformer design in the frequency domain," Journal of Electromagnetic Waves and Applications, vol. 17, no. 2, 2003, pp. 357-381; and X. Li, et al, "Microwave imaging via space-time beamforming: Experimental investigation of tumor detection in multi-layer breast phantoms," *IEEE Transactions on Microwave Theory and Techniques*, vol. 52, no. 8, August 2004, pp.1856-1865. See also U.S. published patent application 2003/0088180 A1, "Space-Time Microwave Imaging for Cancer Detection," published May 8, 2003, the disclosure of which is incorporated by reference.

SUMMARY OF THE INVENTION

Microwave based examination for cancer detection in accordance with the invention overcomes many of the limitations of conventional breast cancer screening modalities. The invention exploits the dielectric-properties contrast between malignant and normal breast tissue at microwave frequencies by taking advantage of the biophysical contrast mechanisms of clinical interest, such as water content, vascularization/angiogenesis, blood flow rate, and temperature, with the potential for sensitivity and resolution sufficient to allow reliable detection of extremely small (millimeter size) malignant tumors even in radiographically dense breast tissue or in the upper outer breast quadrant near the chest wall. The invention utilizes non-ionizing microwave radiation, is non-invasive, does not require the injection of contrast agents, avoids the need for breast compression, and has the potential to reduce the number of false positives associated with conventional X-ray mammography and thereby reduce the number of unnecessary biopsies. Because low-power microwave exposure is harmless, exams may be done more frequently than with X-ray mammography, and monitoring and comparison of breast scans from one exam to the next can be used to identify changes in lesions due to vascularization and the growth of cancerous tissue. Further, discrimination between malignant and benign tumors may also be possible based on spectral and polarization characteristics of benign and malignant tumors. The invention may be implemented utilizing relatively low-cost hardware, allowing reduced cost screening procedures and allowing routine screening to be made more widely available to medically under-served populations in both developed and underdeveloped countries. Further, the safety of imaging techniques, the comfort of the procedure (no breast compression required), the ease of use, and the low cost of the scanning procedure should help to improve acceptance by the public of regular (e.g., annual) screenings.

In hypothesis testing for detecting tumors in accordance with the invention, image data are formed from the test statistic used to perform a binary hypothesis test at each voxel (volume pixel). The null hypothesis asserts that no tumor is present at the corresponding breast location. The voxel threshold is determined by specifying a false discovery rate (FDR) to control the expected proportion of false positives in the image. When the test statistic value associated with a voxel is greater than the threshold, the null hypothesis is rejected and the test statistic is assigned to the voxel. For voxels where the test statistic falls below the threshold, the null hypothesis is accepted and the voxel value is set to zero. The resulting information indicates the locations of detected tumors in the breast, and large values of test statistic at the detected tumor site (which may be represented by a selected color or a darker grey scale value for a pixel on a two-dimensional visual display) suggest relatively high confidence in the decision to reject the null hypothesis.

Data are obtained by sequentially illuminating the breast with an ultrawideband (UWB) pulse or its equivalent and recording scattered time series data of length N in each channel for each of the M antennas in the array. The time series in each channel contains contributions of the following nature: antenna reverberation, reflection from the skin-breast interface, clutter due to the heterogeneous dielectric properties of normal breast tissue, backscatter from possible tumors, and noise. The first two contributions are preferably removed by preprocessing the data with an artifact removal process. After artifact removal, the channel time series of received backscatter is assumed to contain only signal, clutter, and noise components. Space-time vectors for the data y, signal $\alpha cs$ ($\theta$), clutter c, and noise n are formed by stacking the time-series vectors in each channel to obtain $y=\alpha s(\theta)+c+n$, where $\theta$ is a vector of parameters (e.g., location, size, density) that parameterizes the scattering scenario, and $\alpha$ denotes scattering amplitude. If no scatterer is present at a candidate location (i.e., at a selected voxel), then $\alpha=0$. Thus the null hypothesis is $\alpha=0$, while the alternative hypothesis is $\alpha \neq 0$. In general the statistics of the clutter are unknown. It is reasonable to assume the electronic noise is white, although the variance is unknown. Hence, this is a two-sided composite hypothesis test and a uniformly most powerful detector does not exist. The present invention may be carried out utilizing the generalized likelihood ratio test (GLRT).

The GLRT is a test based on likelihood ratios where the unknown parameters are replaced by their maximum likelihood estimates. It is assumed the clutter and noise are zero-mean Gaussian distributed and that the clutter plus noise covariance matrix R is estimated separately. In this case, the GLRT statistic t is the ratio of the sample variances under the two hypotheses (scatterer or no scatterer at the candidate location) and is expressed as $t=(NM-1)(x^T P x)/(x^T P^\perp x)$ where $x=R^{-1/2}y$ is the whitened measured data, $P=R^{-1/2}s(\theta)[s^T(\theta)R^{-1}s(\theta)]^{-1}s^T(\theta)R^{-1/2}$, and $P^\perp=I-P$.

The threshold for the GLRT is selected to control the FDR of an image. The FDR is defined as the expected proportion of falsely rejected null hypotheses in an image. To control the FDR at a given rate, the p-values associated with the hypothesis tests are sorted in ascending order and compared to a line. The largest p-value to fall below the line is taken as the p-value threshold. Then all hypotheses with p-values below or equal to the threshold are rejected. Under the null hypothesis the test statistic can be shown to be central F-distributed. Under the alternative hypothesis, the test statistic is either singly or doubly noncentral F-distributed, and the noncentrality parameters represent the signal to noise ratio and any loss due to mismatch between the assumed signal vector $s(\theta)$ and the true underlying signal vector.

A microwave system that carries out tumor detection in accordance with the invention includes an array of antennas for radiating and receiving microwaves, a microwave source connected to the array of antennas to provide microwave signals such as pulse signals of a selected width and repetition rate to the antennas, and a receiver connected to the antennas to detect the microwave signals received by the antennas and provide signal data corresponding thereto. The system of the invention may also utilize a microwave source which provides the equivalent of a wide bandwidth pulse, such as discrete frequency signals that can be combined to provide the effect of a broadband pulse source or a signal that is swept in frequency (e.g., a frequency "chirp" signal). A computer is connected to receive the signal data and to carry out the hypothesis test processing. The computer is also preferably programmed to carry out artifact removal by estimating an artifact reflection component of a signal at each antenna as a filtered combination of the signals at all other antennas and subtracting the estimated artifact reflection component from the signal data to provide corrected signal data. The weights of the filters are chosen to minimize a residual signal over that portion of the received data dominated by the reflection. The computer is programmed to then carry out hypothesis testing on the corrected signal data as set forth above. An output display device such as a cathode ray tube, LCD screen, etc. may be connected to the computer to display the output as a function of scanned locations, providing an image on which cancerous lesions may be distinguished from surrounding tissue.

Further objects, features and advantages of the invention will be apparent from the following detailed description when taken in conjunction with the accompanying drawings.

Figure 13:
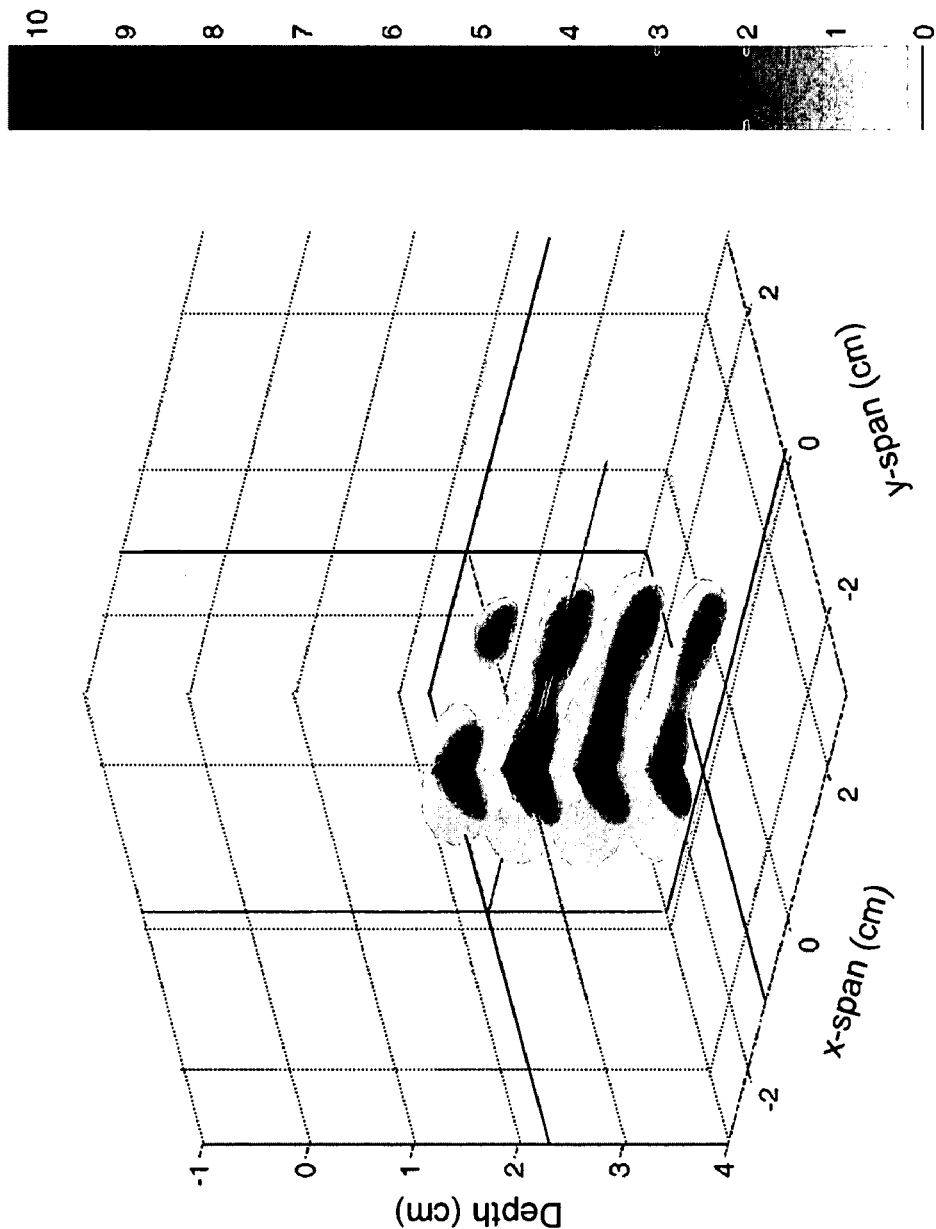

FIG. 13 illustrates a 3-D image of the thresholded test statistics for backscatter from an exemplary 2-tumor physical breast phantom with 4-mm diameter, 4-mm tall cylindrical tumors approximately centered at (−1 cm, 0 cm, 2 cm) and (+1 cm, 0 cm, 2 cm).

Figure 14:
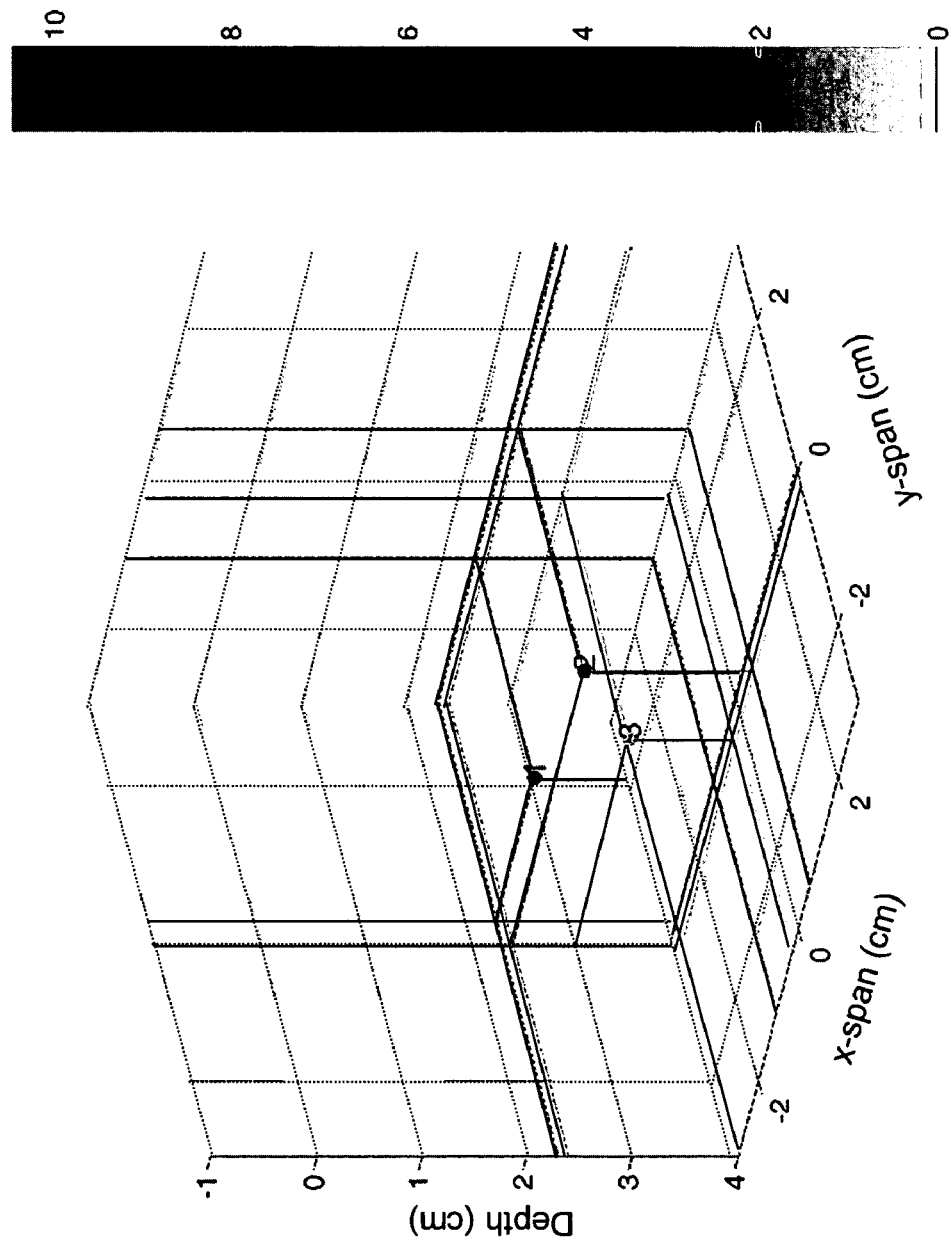

FIG. 14 shows a summary of detected scatterers for the 2-tumor physical breast phantom using an iterative application of the GLRT. The dots numbered 1 through 3 represent the peak test statistic values and locations for iterations 1 through 3, respectively.

Figure 15:
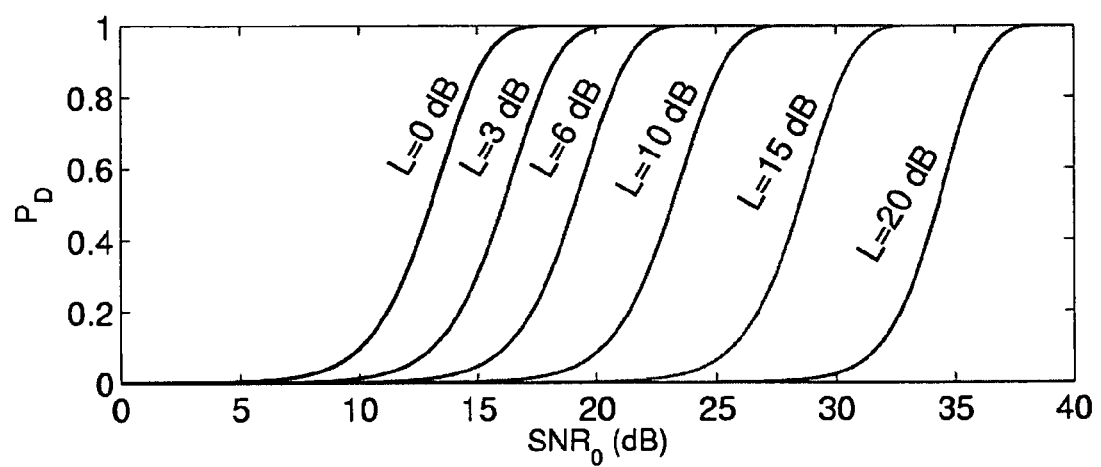

FIG. 15 are graphs illustrating the performance of the GLRT when $P_{FA}=10^{-5}$ and mismatch is introduced, illustrating $P_d$ for several cases of mismatch as a function of signal to noise ratio (SNR).

Figure 16:
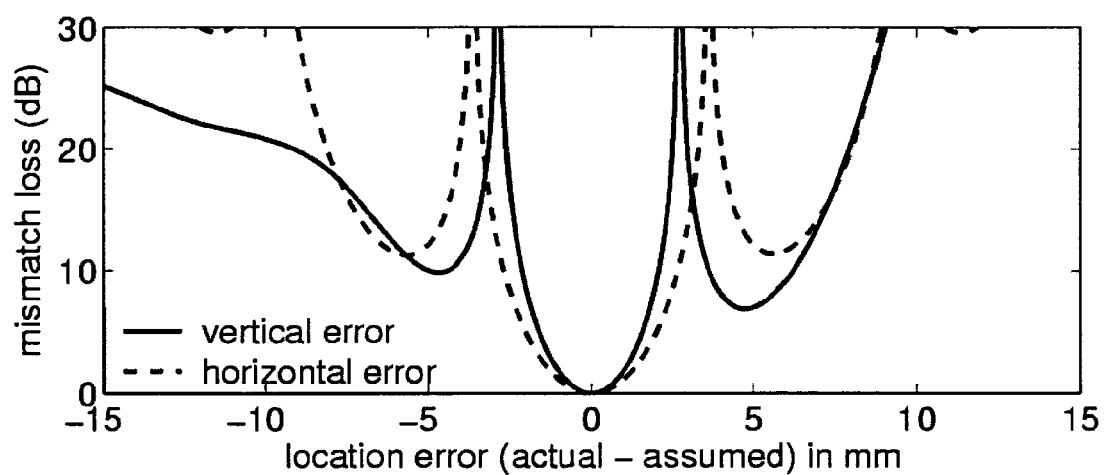

FIG. 16 are graphs illustrating mismatch loss as a function of location error for a test tumor of 2-mm diameter located at (5.0,2.1)cm, with the location error being the horizontal or vertical offset between the true tumor location and the test location.

Figure 17:
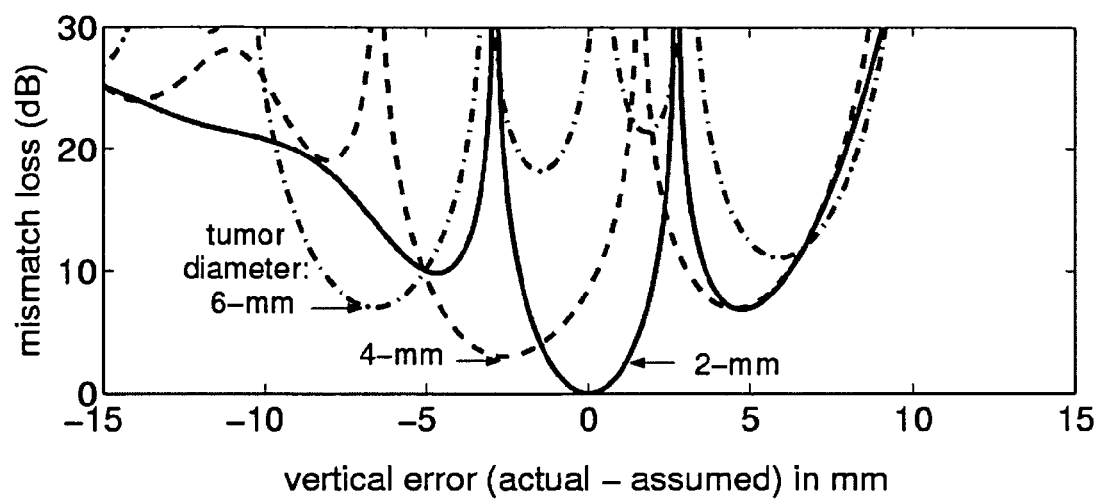

FIG. 17 are graphs illustrating mismatch loss as a function of both tumor location and tumor size for a test tumor having a 2-mm diameter which is centered at (5.0,2.1)cm, while the true tumor diameter and location are varied, with the location errors restricted to offsets along the depth axis.

DETAILED DESCRIPTION OF THE INVENTION

In one embodiment for carrying out the invention, each antenna in an array of antennas sequentially transmits wideband signals providing an effective low-power ultra-short microwave pulse into an object to be examined, such as the breast, and collects the backscatter signal. The relative arrival times and amplitudes of backscattered signals received by the antennas across the antenna array provide information that can be used to detect the presence and determine the location of malignant lesions. Breast carcinomas act as significant microwave scatterers because of the large dielectric-properties contrast with the surrounding tissue. The problem of detecting and localizing scattering objects using pulsed signals and antenna arrays is similar to that encountered in radar systems, such as those used for air traffic control, military surveillance, and land-mine detection.

Data in published literature and from our measurements on freshly excised breast biopsy tissue suggest that the malignant-to-normal breast tissue contrast in dielectric constant, $\epsilon_r$, and conductivity, $\sigma$, is as high as 10:1, depending on the density of the normal tissue. The higher dielectric properties of malignant breast tissue arise, in part, from increased protein hydration and a breakdown of cell membranes due to necrosis. The contrast ratio does not vary significantly with tumor age, which suggests the potential for detecting tumors at the earliest stages of development. Microwaves offer exceptionally high contrast compared to other imaging modalities, such as X-ray mammography, which exploit intrinsic contrasts on the order of a few percent. Data in published literature suggest typical attenuation is less than 4 dB/cm up through 10 GHz, indicating that commercial microwave instrumentation with 100 dB of dynamic range is capable of imaging through 25 cm of tissue. The present invention preferably uses microwave pulses that are on the order of 100 ps in duration, with peak powers on the order of a few milliwatts—approximately 1/100$^{th}$ of the power of a typical cellular phone. Assuming a pulse repetition frequency of 1 MHz and a maximum scan depth of 10 cm, an array of 100 antennas could be sequentially scanned in 0.1 seconds.

The goal of conventional microwave tomography is the recovery of the dielectric-properties profile of an object from measurement of the transmission and scattering of microwave energy through the object. In contrast, imaging in accordance with the invention need be carried out only to identify the presence and location of strong scatterers in the breast. Consequently, the need to solve a challenging, ill-conditioned nonlinear inverse-scattering problem is avoided. Early active microwave backscatter techniques were unsuccessful because they used a single antenna location for transmitting and receiving and thus had no possibility of spatially focusing the backscattered signal. The use of an antenna array and short pulses enables focusing in both space and time, significantly enhancing the response from malignant lesions while minimizing clutter signals, thereby overcoming challenges presented by breast heterogeneity and enabling the detection of lesions as small as 1-2 mm. Resolution is not determined by the wavelength of the microwave excitation. Rather, the spatial extent of the array aperture measured in wavelengths and the temporal duration of the pulse are the dominant factors in determining the resolution limit.

Preliminary measurements suggest that the contrast between the dielectric properties of normal breast tissue and some benign lesions is negligible, in which case benign lesions would not act as strong microwave scatterers, allowing discrimination of benign and cancerous lesions. Furthermore, in contrast to conventional microwave tomography, morphology-dependent characteristics of lesions can be exploited, such as spectral and polarization signatures, as well as the enhanced backscatter due to vascularization of malignant tumors, to further distinguish cancerous lesions from other scattering structures. In addition, change in lesion size is reflected in the backscattered spectral characteristics and signal-to-clutter ratio.

Figure 1:
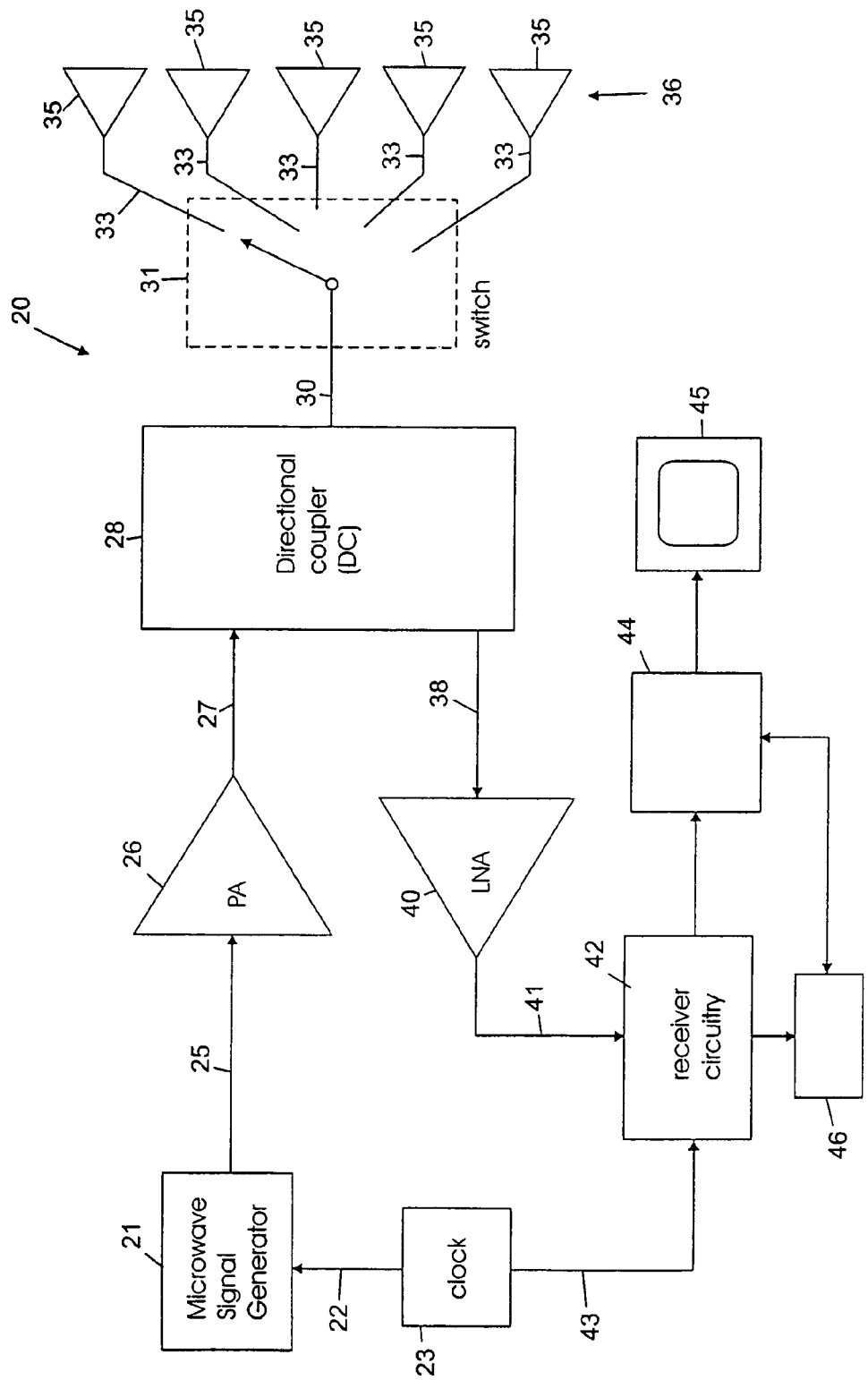
FIG. 1 is a block diagram of a microwave based system in accordance with the invention for transmitting and receiving using the same antenna.

An exemplary microwave examination system which may be utilized in accordance with the invention which provides transmission and reception with the same antenna is shown generally at 20 in FIG. 1. The system 20 includes a microwave signal generator 21 which is supplied, on a line 22, with clock pulses from a clock 23. The output of the signal generator 21, which as described below may be short broadband pulses or an equivalent signal synthesized from multiple discrete frequencies, from a frequency swept (chirp) signal, etc., is provided on a line 25 to a power amplifier 26, the output of which is provided on a line 27 to a directional coupler 28. The output of the directional coupler 28 is provided on a line 30 to a switching system 31 which selectively directs the power from the line 30 to lines 33 leading to each of the antennas 35 which are arranged in an array 36 of antennas (e.g., a rectangular or circular array or other desired geometry). An array of antennas may be effectively provided by using one antenna 35 and moving it from position to position to collect data at each position, although the forming of a "virtual" array in this manner is not preferred. Further, the array may be formed to partially surround the object being imaged: for example, for use in breast imaging the array may be formed to encircle the pendant breast. The antennas 35 and other microwave components should be wideband and preferably operate in the 1-10 GHz range. Examples of wideband antenna designs that may be utilized are the "bowtie" and Vivaldi type antennas and horn antennas designed for wideband operation. See X. Li, et al, "Numerical and experimental investigation of an ultrawideband ridged pyramidal-horn antenna with curved launching plane for pulse radiation," IEEE Antennas and Wireless Propagation Letters, vol. 2, pp. 259-262, 2003. The switch 31 is formed to selectively provide microwave power individually to the antennas 35 from the directional coupler 28 and to receive a signal from that antenna which is directed back through the switch 31 to the directional coupler 28. The directional coupler 28 sends the received signal on a line 38 to a low noise amplifier 40, the output of which is provided on a line 41 to a receiver 42. The receiver 42 also receives clock pulses on a line 43 from the clock 23. The clock pulses on the line 43 allow the receiver 42 to time the onset of pulses of microwave power supplied from the signal generator 21 to allow correlation in time of the received signal with respect to the transmitted signal. Alternatively, the power output from the signal generator 21 may be provided through a power splitter to the receiver 42 to allow time correlation. The signal generator 21, which may include a computer or digital processor, generates appropriately timed and shaped output pulses, discrete frequencies, chirps, etc., as required for the type of microwave transmission being utilized. The receiver 42 may be of conventional construction, providing detection of the received microwave signal and conversion of the detected signal to digitized data, e.g., with sampling of the received signal after each pulse to build up a digitized waveform, with the digitized data being provided to a digital signal processor of conventional design within the receiver 42 or to an appropriately programmed computer 44 (e.g., a general purpose PC, a dedicated digital signal processor, etc.) all of which will be referred to herein generally as a "computer." It is understood that any type of computer that can be programmed to carry out the signal/data processing set forth herein may be utilized. The receiver 42 or the separate computer 44 processes the data to provide image data which may be displayed on a display device 45, such as a video display terminal, or which may be transmitted to a recording device 46 such as a magnetic disk or CD ROM for long-term storage, or transmitted for printout, further data processing, etc. In accordance with the invention, detection of tumors using hypothesis testing is carried out in a computer in the receiver 42 or a separate computer 44 on the data received from the antennas, as described further below. Further, signal processing is preferably employed to carry out a reflection artifact subtraction process (e.g., for the skin interface response or the antenna response) to reduce the effect of the artifact response on the received image data. The system of the invention may be implemented with equipment specially constructed for the purpose of the invention or with commercial equipment such as vector network analyzers or their equivalent. As an example only of commercial instruments that may be utilized, the signal generator 21, amplifiers 26 and 40, directional coupler 28, receiver 42 and clock 23 may be implemented in an Agilent Performance Network Analyzer model E8364A, particularly for the discrete frequency based approach, and the computer 44 may be connected to control the signal generator 21 and the switch 31.

Figure 2:
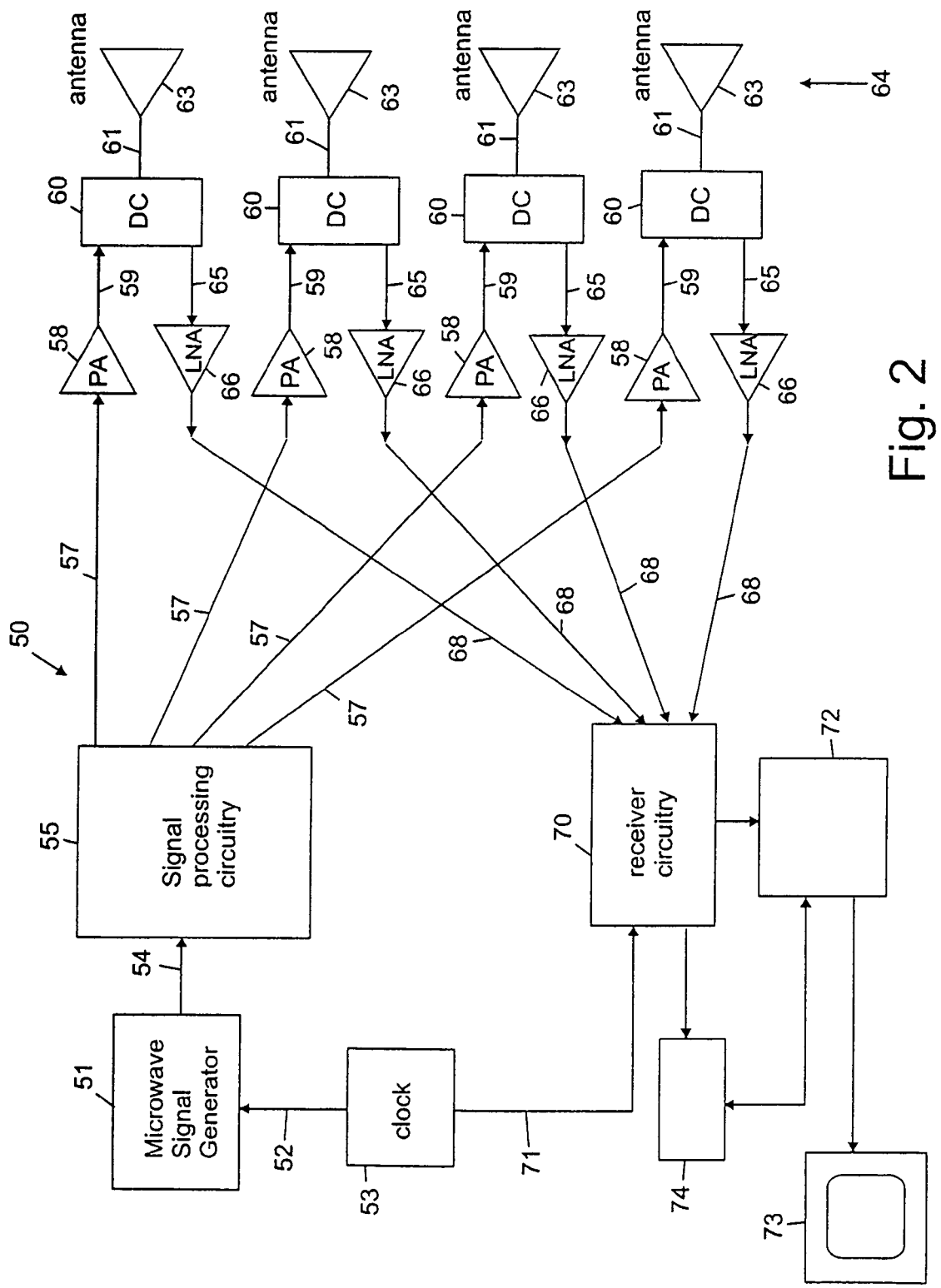
FIG. 2 is a block diagram of a further embodiment of a microwave system in accordance with the invention providing simultaneous transmission and reception with all antennas.

A system in accordance with the invention which may be utilized for simultaneous transmission from each antenna is shown generally at 50 in FIG. 2. The system 50 includes a signal generator 51 which receives a clock pulse on a line 52 from a clock 53. The output of the signal generator 51 is provided on a line 54 to signal processing circuitry 55 which distributes the microwave (e.g., pulse) output on lines 57 to power amplifiers 58. Each of the power amplifiers 58 provides its output on a line 59 to a directional coupler 60, the output of which is provided on a line 61 to an individual antenna 63. The antennas 63 are arranged to form an array 64 of antennas, e.g., a rectangular array of antennas arranged in rows and columns, and non-rectangular or non-planar arrays may also be utilized. The signal processing circuitry 55 distributes the pulse of microwave or its equivalent on each of its output lines 57 with frequency dependent filtering to provide the desired microwave radiation from the antenna array 64, e.g., focusing of radiated power from the array 64 to selected points in the target object. The signals picked up by each antenna 63 are transmitted back on the line 61 to the directional coupler 60. The directional couplers provide the received signals on lines 65 to low noise amplifiers 66, the outputs of which are provided on lines 68 to a receiver 70. The receiver 70 also receives the clock pulses from the clock 53 on a line 71 to allow the receiver 70 to time the received signals with respect to the transmitted signals. The receiver 70 detects the microwave signal on a line 68 and converts the received signal to digital waveform data which is processed by a digital signal processor or a computer 72 in accordance with the invention. The image data from the computer 72 or digital signal processor may be displayed, e.g., on a video display terminal 73, or provided to a storage device 74, e.g., CD ROM, magnetic disk, tape, etc. for long-term storage, or transmitted for other purposes.

Figure 3:
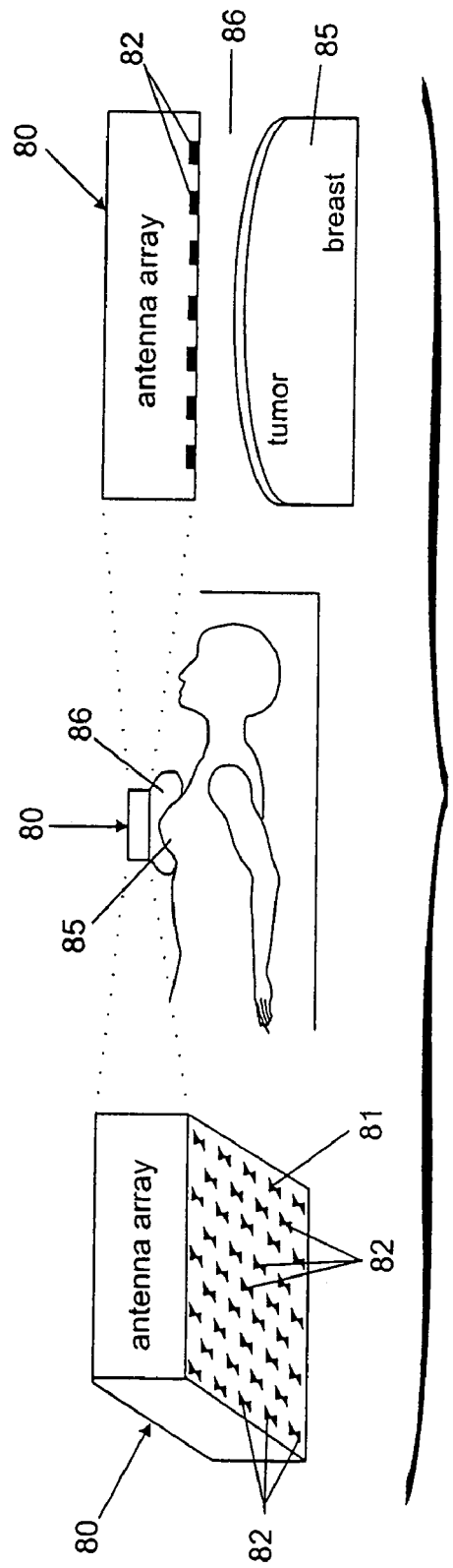
FIG. 3 is an illustrative view of an antenna array and its utilization in the present invention.

With reference to FIG. 3, an antenna array device which may be utilized in the system of the invention is shown generally at 80, having a face 81 over which are distributed multiple individual antennas 82 arranged in a two-dimensional array at known locations. The individual antenna elements 82 may have the "bow-tie" shape as shown or any other shapes as desired, as discussed above. The array device 80 may be utilized as the antenna array 36 of FIG. 1, with the antenna elements 82 corresponding to the antennas 35, or as the antenna array 64 of FIG. 2, with the antenna elements 82 corresponding to the antennas 63. For purposes of illustration, the antenna array device 80 is also shown in FIG. 3 placed adjacent to the breast 85 or other portion of the body to be imaged, preferably utilizing a matching element 86, such as a liquid filled bag, which conforms to the contour of the breast or other part of the body being imaged to minimize air gaps and unwanted reflections of microwave energy. It is understood that FIG. 3 is presented for illustration only, and other arrangements may be used, e.g., an array of antennas encircling the breast of a prone patient. While the invention is illustrated herein with regard to breast imaging, it is understood that the present invention may be utilized for examining other parts of the body of an individual.

To achieve the best resolution of the reconstructed image, the radiated microwave pulse is preferably relatively short (e.g., about 100 ps), and thus has a wideband of frequency content, typically from 0 to 20 GHz and with significant energy in the frequency range of 1 GHz to 10 GHz. It is understood that as used herein, signals equivalent to a short, wideband pulse may be used and are included within any reference to pulse excitation herein. Such equivalent signals are known to those of ordinary skill, and include, for example, multiple serially applied discrete frequency signals and frequency chirped signals. Thus, it is desirable to utilize antennas that are suitable for transmitting and receiving such short pulses or equivalent wideband signals with minimum distortion or elongation. It is desirable that the pulse radiating antenna have a constant sensitivity and a linear phase delay over the bandwidth of the incident electromagnetic pulse in the frequency domain. It is also desirable that the antenna design suppress both feed reflection and antenna ringing, and that the antenna have a smooth transition from the cable impedance at the feed point to the impedance of the immersion medium at the radiating end of the antenna. The return loss should be low in magnitude as less return loss means more power is transmitted to the antenna. Ideally, the return loss should be constant over the required bandwidth so that the spectrum of the transmitted power is flat and should have a linear phase delay across the frequency band so that the radiated waveform will not be dispersed. Other desirable properties include a well-defined polarization, constant gain, and low side lobes in the radiation pattern. Resistively loaded cylindrical and conical dipole (monopole), and bow-tie antennas can be utilized for radiating temporally short, broad bandwidth pulses. Resistive loading can be utilized to reduce the unwanted reflections that occur along the antenna and the associated distortion of the radiated signal. Spiral antennas and log-periodic antennas have also been designed to achieve wide bandwidth. Spectrum shaping and RF filtering may be needed to enhance the frequency performance of these antennas. Specialized antennas designed for pulse radiation may also be utilized. An example of a suitable antenna that is designed for short pulse radiation is shown and described in U.S. Pat. No. 6,348,898, issued Feb. 19, 2002.

Figure 7:
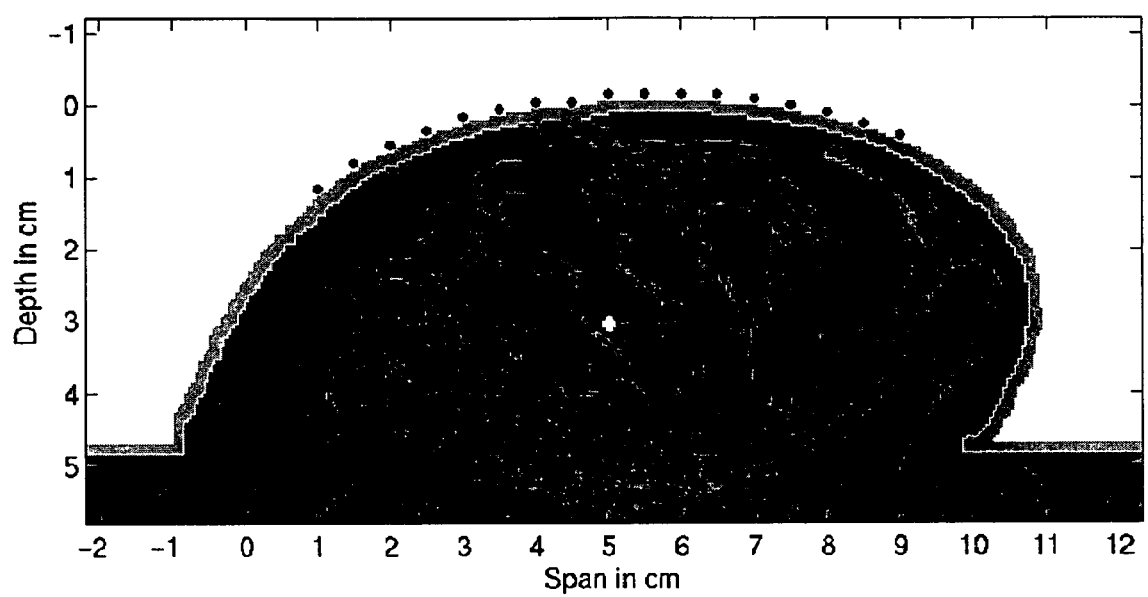
FIG. 7 is an exemplary two-dimensional (2-D) numerical model of a heterogeneous breast with a 2 mm diameter tumor centered in the figure at (5.0,3.1)cm, with the dots on the skin surface representing antenna positions.

As an example, the present invention was applied to simulated backscatter data generated from finite-difference time-domain (FDTD) computational electromagnetics simulations of microwave propagation in the breast. The anatomically realistic breast model was derived from a high-resolution 3-D breast MRI (magnetic resonance imaging) obtained during routine patient care at the University of Wisconsin Hospital and Clinics. The face-down images of the pendant breast were digitally rotated, vertically compressed, and laterally expanded to create high-resolution images of the naturally flattened breast of a patient in a supine position as illustrated in FIG. 7. Then, each voxel was assigned the appropriate values of $\in_r$ and $\sigma$. The 2-D model is incorporated into FDTD simulations for a co-linear 17-element monopole antenna array spanning 8 cm along the surface of the breast (with the antenna elements shown by the black dots in FIG. 7). Each antenna is excited with an ultrashort differentiated Gaussian pulse (temporal width of 110 ps, bandwidth of 9 GHz) and the backscattered response at the same antenna element is computed. This process is repeated for each element of the array, resulting in 17 received backscattered waveforms. The resulting FDTD-computed backscatter waveforms represent the scattering effects of the skin-breast interface (artifact), heterogeneous normal breast tissue (clutter) and the malignant tumor (signal).

The skin response subtraction process estimates the skin component of the signal at each antenna as a filtered combination of the signals at all other antennas. The filter weights are chosen to minimize the residual signal over that portion of the received data dominated by the reflection from an interface with the object being imaged such as the skin-breast interface. The results show that the skin response effect is removed at the expense of energy from the tumor bleeding throughout the image. This occurs because the skin response subtraction algorithm used somewhat distorts the response from the tumor.

Removal of the response from the skin-breast interface is critical for lesion detection, as this response is orders of magnitude larger than the tumor response. This response may be removed at the expense of some distortion of the tumor response. The distortion is known since it is a function of the weights used for skin response removal, allowing processing to be carried out for reducing or eliminating the tumor response distortion.

The skin response removal algorithm estimates the skin response at each antenna. The skin response is a known function of the skin thickness and the dielectric properties of the skin and breast. This fact may be exploited in processes for estimating these properties from the skin response. The average breast dielectric properties may then be used as a calibration step to choose the best system design for each patient.

The methods described above assume only one antenna is transmitting and receiving at any point in time. This process involves sequentially stepping through the array. If an antenna array with multiple receive channels is used, as shown in FIG. 2, then a multitude of different transmit-receive strategies are possible. Hypothesis testing and skin response removal algorithms may be utilized in which all antennas receive simultaneously. Transmit strategies may also be utilized that focus the transmitted energy on a given region of the breast. The transmit and receive focus location is then scanned throughout the breast to form the image of statistically significant scatterers. Such scanning may be utilized to improve resolution and robustness to artifacts, noise, and clutter. The signal parameters used to focus the transmission are the relative transmit time and signal amplitude in each antenna. Effective focusing may also be carried out by software processing of the received signal data without actual focusing of the transmittal microwaves. After a lesion is located, if appropriate, the transmitted energy from the antennas may be focused on the lesion at a higher power level to heat and destroy the lesion.

Methods may be employed for assessing changes in lesion size from images obtained at different points in time. Both the spatial extent of the scattering region as well as the total power returned may increase from one scan to the next if the tumor undergoes angiogenesis and growth. Tracking this growth would be useful in the diagnosis of malignant lesions. Both the spatial extent of the scattering region and the total power returned may decrease if cancerous cells in the lesion are destroyed. Monitoring the decrease in lesion size would aid in assessing the effect of radiation therapy, chemotherapy, and/or thermotherapy. Use of absolute estimated tumor power is problematic due to expected variation from one measurement to the next. Frequency dependent scattering effects will also vary with tumor size and provide another means for assessing changes over time.

An exemplary sensor in the imaging system of the invention may include a microwave vector reflectometer (the pulse generator 21, 51 and receiver 42, 70, and may include the associated amplifiers and directional couplers) and a low-reverberation ultrawideband transmitting/receiving antenna. A low-noise commercial vector network analyzer (VNA) with a time-domain option may be used for the vector reflectometer. The dynamic range of a VNA of this type is sufficient to detect small malignant tumors up to depths of 5.0 cm in the breast.

The strategy for detection is to identify the presence and location of strong scatterers in the breast, rather than to attempt to reconstruct the dielectric-properties profile of the breast interior. As a result, the approach overcomes the fundamental computational limitations and related vulnerabilities to noise of conventional narrowband microwave tomography. The use of spatial and temporal focusing can enhance the response from malignant lesions while minimizing clutter signals, thereby overcoming challenges presented by breast heterogeneity. Space-time focusing achieves super-resolution, enabling the detection of extremely small (<5 mm in diameter) malignant lesions with harmless low-power microwave signals. The need for breast compression is eliminated, and the breast tissue can be imaged with the patient lying comfortably on her back. This enables detection of tumors located near the chest wall or in the quadrant near the underarm where an estimated 50% of all breast tumors occur.

Reflection artifact removal (such as skin response removal), and detection of tumors by hypothesis testing in accordance with the invention are discussed in further detail below. These processes may be carried out in a separate computer (e.g., the computer 44 of FIG. 1 or 72 of FIG. 2), or in a digital signal processor of the receiver (e.g., the receiver 42 of FIG. 1 or the receiver 70 of FIG. 2), both of which will be referred to herein as a computer, that is programmed to carry out the processing on the digitized waveform signal data for each antenna that is provided by the receiver.

The following describes the artifact removal and hypothesis testing methods in mathematical expressions which are implemented in the computer and/or digital signal processors of the systems of FIGS. 1 and 2. Lower and upper case boldface Roman type is used to denote vector and matrix quantities, respectively. Superscript * represents the complex conjugate and superscripts T, H, and −1 represent the matrix transpose, complex conjugate transpose, and inverse, respectively.

Reflection Artifact Subtraction

A reflection artifact removal process is preferably carried out on the data received from the antennas to remove large reflection artifacts, such as the energy reflected from the ends of the antenna and feed and from the skin-breast interface. These reflections are typically orders of magnitude greater than the received backscatter signal. This reflection artifact removal or subtraction process will be described below for the example of removal of the skin-breast interface response. The skin response removal process forms an estimate of the response associated with the skin-breast interface and subtracts it from the recorded data.

The following discusses the preferred solution of the skin response removal problem in further detail. See also E. J. Bond, et al., August 2003, supra and published patent application 2003/0088180 A1.

Consider an array of N antennas and denote the received signal at the $i^{th}$ antenna as $b_i(t)$. Each received signal is converted to a sampled waveform, $b_i[n]$, by an A/D converter in the receiver operating at a sampling frequency $f_s$. The received signal contains contributions from the skin-breast interface, clutter due to heterogeneity in the breast, the backscatter from lesions, and noise. The response from the skin-breast interface is orders of magnitude larger than the response from all other contributions and thus must be removed prior to performing tumor detection.

Figure 4:
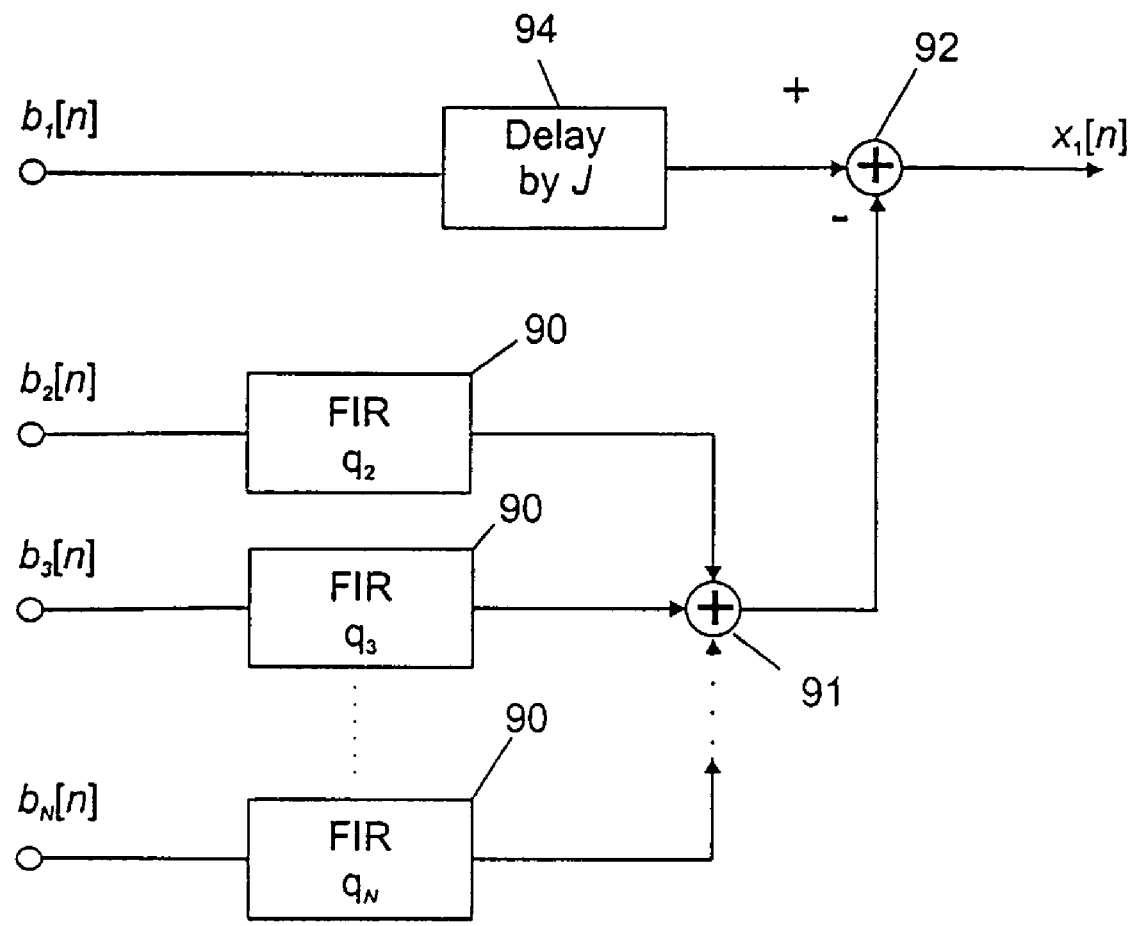
FIG. 4 is a block diagram illustrating the process of artifact removal from a backscattered signal at the first antenna (antenna 1).

The skin artifacts in each of the N channels are similar but not identical due to local variations in skin thickness and breast heterogeneity. If the skin artifact for all channels were identical, one approach to remove it would be to subtract the average of the skin artifact across the N channels from each channel. In order to compensate for channel to channel variation in the skin artifact, the skin artifact at each antenna may be estimated as a filtered combination of the signal at all other antennas, as shown in FIG. 4. The signals from each of the other antennas are provided to FIR (finite impulse response) filters 90, the outputs of which are summed at 91 and subtracted at 92 from the signal from the particular antenna after a delay 94. The filter weights of the FIR filters 90 are chosen to minimize the residual signal mean-squared error over that portion of the received data dominated by the reflection from the skin-breast interface. Without loss of generality, suppose that the skin artifact is to be removed from the first antenna. Define the $(2J+1)\times 1$ vector of time samples in the $i^{th}$ antenna channel as $$b_i[n]=[b_i[n-J], \ldots, b_i[n], \ldots, b_i[n+J]]^T, 2 \le i \le N \quad (1)$$

and let $b_{2N}[n]=[b_2^T[n], \ldots, b_N^T[n]]^T$ be the concatenation of data in channels 2 through N. Similarly, let $q_i$ be the $(2J+1)\times 1$ vector of FIR filter coefficients in the $i^{th}$ channel and $q=[q_2^T, \ldots, q_N^T]^T$ be the concatenation of FIR filter coefficients from channels 2 through N. The optimal filter weight vector is chosen to satisfy $$q = \arg\min_q \sum_{n=n_0}^{n_0+m-1} |b_1[n] - q^T b_{2N}[n]|^2 \quad (2)$$

where $n_0$ is the time that approximates when the skin artifact begins and m is the duration of the received signal that is dominated by the skin artifact. The solution to this minimization problem is given by $$q = R^{-1} p \quad (3)$$

$$R = \frac{1}{M} \sum_{n=n_0}^{n_0+m-1} b_{2N}[n] b_{2N}^T[n] \quad (4)$$

$$p = \frac{1}{M} \sum_{n=n_0}^{n_0+m-1} b_{2N}[n] b_1[n] \quad (5)$$

The fact that there is a high degree of correlation among the skin artifacts in the N channels results in the sample covariance matrix R being ill-conditioned. If R is ill-conditioned, then the matrix inversion in equation (3) can result in a solution for q that has very large norm and thus amplifies noise. In order to prevent this, we replace R with the low rank approximation $$R_p = \sum_{i=1}^{p} \lambda_i u_i u_i^T \quad (6)$$

where $\lambda_i$, $1 \le i \le p$, are the p significant eigenvalues and $u_i$, $1 \le i \le p$, are the corresponding eigenvectors. The filter weight vector is determined by replacing $R^{-1}$ in equation (3) with $$R_p^{-1} = \sum_{i=1}^{p} \frac{1}{\lambda_i} u_i u_i^T \quad (7)$$

The skin artifact is then removed from the entire data record of the first channel to create artifact free data $x_1[n]$ given by $$x_1[n]=b_1[n]-q^T b_{2N}[n] \quad (8)$$

This algorithm introduces a small level of distortion in the backscattered lesion signal because the backscattered lesion signals from the other N−1 channels are added back in to the first channel. This is explicitly shown by decomposing $b_1[n]$ and $b_{2N}[n]$, into a skin artifact $s_1[n]$ and $s_{2N}[n]$ and residuals $d_1[n]$ and $d_{2N}[n]$, respectively. The residual signals contain the backscattered response from the lesion. The values $n_0$ and m are chosen so that q is determined from a portion of the data in which the residuals are negligible and, thus, $$s_1[n]-q^T s_{2N}[n] \approx 0 \quad (9)$$

However, decomposing $b_1[n]$ and $b_{2N}[n]$ in equation (8) gives $$x_1[n]=s_1[n]-q^T s_{2N}[n]+d_1[n]-q^T d_{2N}[n] \quad (10)$$

$$\approx d_1[n]-q^T d_{2N}[n] \quad (11)$$

Figure 5:
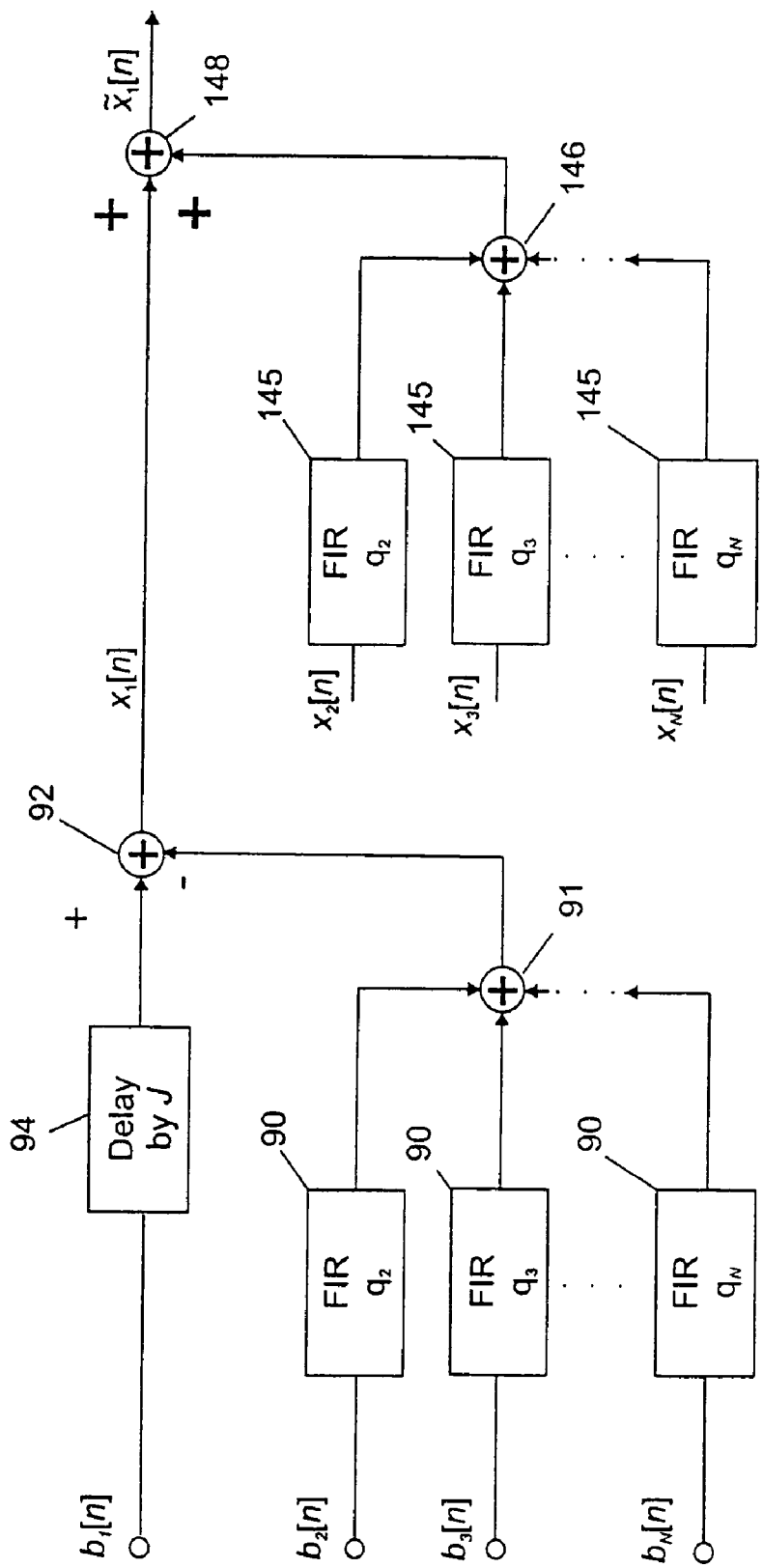
FIG. 5 is a block diagram as shown in FIG. 4 with the addition of a component to reduce distortions from the skin response removal process.

Thus, the residual signal is distorted by $q^T d_{2N}[n]$. This term is generally small because q tends to "average" across channels and the lesion responses in $d_{2N}[n]$ do not add in phase because they are not aligned in time. A simple method for reducing the distortion is to add a filtered version of the residual to obtain $$\tilde{x}_1[n] = x_1[n] + q^T x_{2N}[n] \quad (12)$$

where $$x_{2N}[n] = [x_2[n-J], \ldots, x_2[n+J], \ldots, x_N[n-J], \ldots, x_N[n+J]]^T \quad (13)$$

is the vector containing the data from the other N−1 channels after the skin artifact has been removed from each of them. This addition of a filtered form of the residual is illustrated in FIG. 5 which includes FIR filters 145 to provide filtered signals that are summed at 146 to produce a signal added at 148 to the corrected data signal $x_1[n]$ to provide an improved corrected signal data $\tilde{x}_1[n]$.

Figure 6:
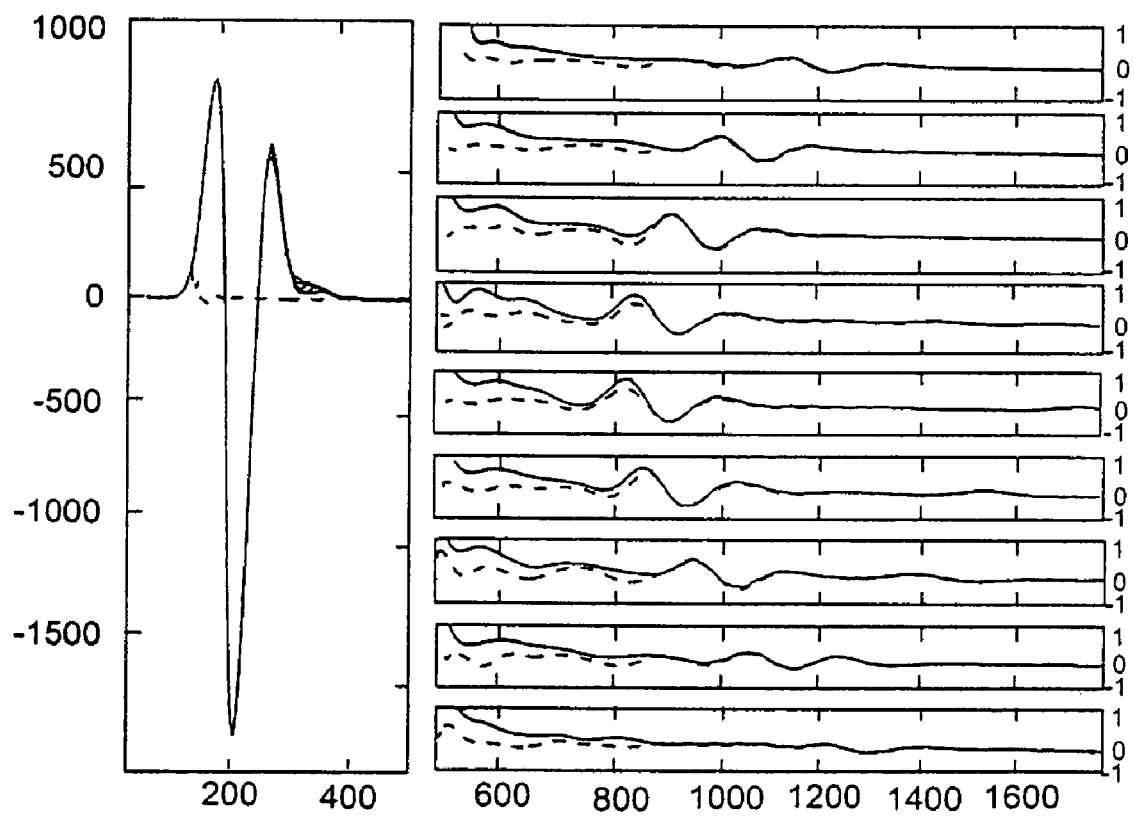
FIG. 6 are time waveforms showing skin artifact removal, with the solid curve showing the original waveforms and the dashed curves corresponding to the waveforms after application of the skin artifact removal algorithm.

FIG. 6 are example waveforms showing the effect of the skin response subtraction process, with the solid lines indicating the original waveforms and the dashed lines indicating the waveforms after skin artifact removal.

The artifact subtraction process can be applied only in the time domain. Thus, if frequency scanning is carried out using multiple discrete frequencies as the signals applied to the antennas, rather than wideband pulses, the received signal data must first be converted to the time domain (using an inverse FFT) prior to applying the artifact subtraction process.

The artifact removal process requires that all of the artifacts occur at the same relative times in the different channels. If the antennas are located at varying distances from the skin, the skin response will occur at different times. Thus, to apply the algorithm in general, the waveforms must first be time shifted so artifacts in all channels occur simultaneously. Aligning the artifacts in time is trivial because by nature the artifact is huge and it is easy to see when it starts.

The antenna reflection response will not vary in time in the different channels (assuming nearly identical antennas), so time alignment is not needed for removing it. The algorithm can simultaneously remove antenna artifact and skin reflection artifact, provided they are both time aligned in the waveforms. While this is true if the array is on the surface of the skin, it is not generally true if the distances to the skin differ for different antennas. In this case, one can apply the algorithm twice: first, to remove the antenna response, followed by time alignment of the residual skin response and, second, to remove the skin response.

There is one limitation with applying it twice, and that has to do with the other requirement of the algorithm, which requires the artifact to be the only contribution to the signal over a time interval that spans at least part of the artifact duration. Hence, if the antennas are varying distances from the skin, but in some channels the skin response completely overlaps (in time) the antenna response, it may not perform adequately.

Hypothesis Testing

In the present invention, observations are obtained by transmitting an UWB pulse or an equivalent into the breast and recording backscattered data in M channels (where there are M antennas). An observation vector $y_i$, denoting the length-N time series from channel i, contains reflections from the skin-breast interface, clutter due to heterogeneity in the breast, backscatter from possible tumors, and noise. The response from the skin-breast interface can be ignored since it can be effectively eliminated by estimating the skin-breast response in channel i as a filtered combination of all other channels and subtracting this estimate from the observed data as discussed above. Thus, neglecting the skin-breast response, the observation vector at channel i for the case of a scatterer (malignant tumor) parameterized by $\theta_{l_0}$ has the following form, $$y_i = \alpha_{l_0} s_i(\theta_{l_0}) + c_i + n_i \quad (14)$$

where $\theta_l$ denotes the $l^{th}$ vector for parameterizing the physical scattering scenario and $l_0$ corresponds to the true scattering scenario for the received backscatter. The signal vector $s_i(\theta_{l_0})$ denotes a normalized time series of the backscatter signal in channel i due to the scattering scenario parameterized by $\theta_{l_0}$. If no scatterers are present then the scale factor $\alpha_{l_0}$ is zero. $c_i$ and $n_i$ are the clutter and noise, respectively, in channel i. Space-time column vectors for the data and signal are formed by stacking the time-series column vectors of backscatter received in each channel, that is $y = [y_1^T\ y_2^T \ldots y_M^T]^T$ and $s(\theta_l) = [s_1^T(\theta_l)\ s_2^T(\theta_l) \ldots s_M^T(\theta_l)]^T$. Space-time column vectors for the noise and clutter are formed in the same manner. Lower and upper case boldface symbols denote vectors and matrices, respectively, while superscripts T and −1 denote the matrix transpose and inverse, respectively. The parameterization of the backscattered signal denoted by $\theta_{l_0}$, may describe any relevant features of the scattering problem including the scatterer location, size, shape and density. For ease of exposition, assume that scatterer location is the sole parameter, that is $\theta_l = r_l$, $l = 1, 2, \ldots, L$ where $r_l$ denotes the $l^{th}$ scatterer location from a set of L locations scanned over the breast and formulate a series of binary hypothesis tests where the null hypothesis $H_l$ states that no tumor is present at location $r_l$: $H_l$: $\alpha_l \neq 0$ vs. $A_l$: $\alpha_l = 0$. Each location is tested independently of all other locations. This strategy is appropriate for detecting single tumors or multiple tumors that are spatially separated assuming negligible interaction between them. That is, in the multiple tumor case we assume scattering effects are approximately linear. This is a reasonable assumption for clinical applications since we are not concerned with distinguishing two tumors that occur very close together in the breast.

For the $l^{th}$ hypothesis test, assume that the signal vector $s(\theta_l)$ is deterministic and perfectly known, but the deterministic scale factor $\alpha_l$, is unknown. The random clutter and noise vectors are assumed to be Gaussian distributed as $c+n \sim N(0, \sigma^2 R)$ where the covariance structure R is known but the power level $\sigma^2$ of these components is unknown. The backscatter data and signal vectors are whitened by the following transformations:

$$x = R^{-1/2} y \quad (15)$$

$$u(\theta_l) = R^{-1/2} s(\theta_l). \quad (16)$$

Then the GLRT test statistic for the the $l^{th}$ test is given by the ratio of the unbiased variance estimates under the null and alternative hypotheses $$t_l = \frac{\hat{\sigma}^2|H_l}{\hat{\sigma}^2|A_l} = (NM-1)\frac{x^T P_l x}{x^T P_l^{\perp} x} \begin{matrix} A_l \\ > \\ < \\ H_l \end{matrix} \eta \quad (17)$$

where the projection matrix $P_l = u(\theta_l)[u^T(\theta_l)u(\theta_l)]^{-1} u^T(\theta_l)$ projects onto the one-dimensional subspace spanned by the whitened signal vector and the orthogonal projection matrix $P_l^{\perp} = I_{NM} - P_l$ projects onto the (NM−1)-dimensional complementary subspace.

The threshold η is chosen to satisfy a specified false discovery rate (FDR) for the image. Under hypothesis $H_{l_0}$ (corresponding to the true scattering parameters of the data, $\theta_{l_0}$), the test statistic $t_l$ is known to be centrally F-distributed, while under the alternative hypothesis $A_{l_0}$, $t_l$ is noncentrally F-distributed with noncentrality parameter $\delta_0$. In both cases the degrees of freedom are $v_1=1$ for the numerator and $v_2=NM-1$ for the denominator. This detector has a constant false alarm rate (CFAR) since the threshold is only dependent on the dimensions N and M of the data.

An image of detected scatterers is constructed by applying the GLRT for all locations l=1,2, . . . ,L and plotting the thresholded test statistic as a function of location. In addition to detecting and localizing scatterers, the GLRT can be modified to classify additional tumor features by further parameterizing the signal vectors with other relevant characteristics such as tumor diameter, tumor shape, tumor density, and normal breast tissue density. For each additional parameter, GLRT images are constructed to test how well the data is described by a finite set of representative values for that parameter. Then a classification test can be applied to the images to make inferences about the underlying scattering characteristics.

Normal breast tissue consists of a heterogeneous mixture of fatty, fibrous, connective and glandular tissue. Clutter naturally arises in the backscatter data in the form of reflections of the incident pulse due to the heterogeneity of normal breast tissue. The clutter can be modeled as a Gaussian random process corresponding to a simplified scattering scenario and the corresponding model correlation matrix can be used to whiten data prior to applying the GLRT.

For a fixed channel i, the clutter in the backscatter is modeled as a weighted sum of the incident pulse at discrete delays. We assume that the delays are fixed and uniformly spaced at integer multiples of the sample period, and that the weights at each delay are zero-mean Gaussian random variables. Let $\gamma_i[k]$ denote the real-valued Gaussian coefficient for channel i at delay k, and assume $E\{\gamma_i[k]\gamma_i[l]\}=0$ for $k\neq l$. The coefficient variance, $\sigma_c^2[k]=E\{\gamma_i[k]^2\}$ (identical for all channels), decays exponentially as a function of k because of the attenuation of electromagnetic waves propagating in breast tissue (the attenuation constant of normal breast tissue is estimated to be a few dB/cm in the microwave frequency range). As a consequence of the exponential decay, the number of non-negligible coefficients, K, is finite. If p[n] represents the incident pulse at sample n, then the clutter in channel i at sample n is modeled as $$c_i[n] = \sum_{k=1}^{K} \gamma_i[k]p[n-k]. \quad (18)$$

Modeling the clutter in this fashion for each channel, we make the additional assumption that the weights in each channel are uncorrelated, $E\{\gamma_i[k]\gamma_j[l]\}=0$ for $i\neq j$, $k\neq l$. This assumption relies on the attenuation of the propagating microwaves since the clutter in each channel is dominated by the heterogeneity in the immediate vicinity of each antenna. The temporal clutter correlation matrix $R_c=E\{c_i c_i^T\}$, identical for all channels, is thus given by $$[R_c]_{nm} = E\{c_i[n]c_i[m]\} = \sum_{k=1}^{K} \sigma_c^2[k]p[n-k]p[m-k]. \quad (19)$$

Note that if the number of significant coefficients, K, is less than N (the dimension of $R_c$), then the clutter covariance matrix will be ill-conditioned. The clutter model described here is analogous to a wide-sense stationary communication channel that is frequency selective with uncorrelated scattering.

Clutter whitening transformations are performed on a channel-by-channel basis with regularization parameter A to obtain whitened data $x_i=(R_c+\lambda I)^{-1/2}y_i$ for all i. Thus the covariance matrix R of eqn.'s (15) and (16) is block diagonal where each of the blocks on the diagonal is given by the matrix $R_c+\lambda I$. Since white noise is also assumed to be present in the observed vectors, this regularized matrix inversion gives a true whitening transformation of the clutter-plus-noise component when λ coincides with the noise power. The signal vectors $s_i(\theta_l)$ are similarly whitened to account for the signal distortion associated with whitening.

Simulations of the invention were carried out on simulated backscatter data generated as discussed above by a Finite-Difference Time-Domain (FDTD) solution of Maxwell's equations to provide the numerical breast model shown in FIG. 7. The FDTD model is derived from a magnetic resonance image (MRI) where each pixel intensity in the MRI is linearly mapped to a range of dielectric properties about a nominal value and a 2-mm-diameter malignant tumor is introduced at (5.0, 3.1) cm by changing the dielectric properties to match those of malignant tissue. The FDTD model is 2-D, and thus the values depicted in FIG. 7 extend infinitely in a third spatial dimension so that the malignant tumor is represented by an infinite-length cylinder. A conformal 17-element antenna array is assumed to rest on the skin surface as indicated by the black dots in FIG. 7. Each antenna array element sequentially transmits a differentiated Gaussian pulse with a duration of approximately 110 ps, and records 125 time samples of backscatter at a sample period of 20 ps.

The clutter covariance matrix model is constructed as specified above where $\sigma_c^2[k]$ is obtained as the maximum likelihood estimate of the clutter power from 51 tumor-free ($\alpha_{l_0}=0$) FDTD solutions. Calculations are performed assuming that the incident pulse is a unit amplitude impulse:

$$\hat{\sigma}_c^2[k] = \frac{1}{51}\sum_{i=1}^{51} (y_i[k] - \bar{y}[k])^2$$

where $\bar{y}[k]=\Sigma_{j=1}^{51}y_j[k]$. The clutter correlation matrix is ill-conditioned so we choose the regularization parameter λ approximately 4 orders of magnitude smaller than the peak estimated clutter power.

Two-dimensional analytical templates are used as the set of signal vectors $\{s(\theta_l), l=1,2, \ldots ,L\}$ for the GLRT, and are obtained by modeling the 2-D tumor as an infinite-length cylinder of given diameter centered at test location $r_l$ in a homogeneous medium representing normal breast tissue. The dielectric properties of the cylinder and surrounding medium are assigned the average dielectric properties of malignant and normal breast tissue, respectively, at 6 GHz. For the following examples, the signal templates are computed for a 2-mm diameter tumor and the location parameter r samples the interior of the breast at 1-mm intervals. We specify the probability of false alarm as $P_{FA}=10^{-5}$.

Figure 8:
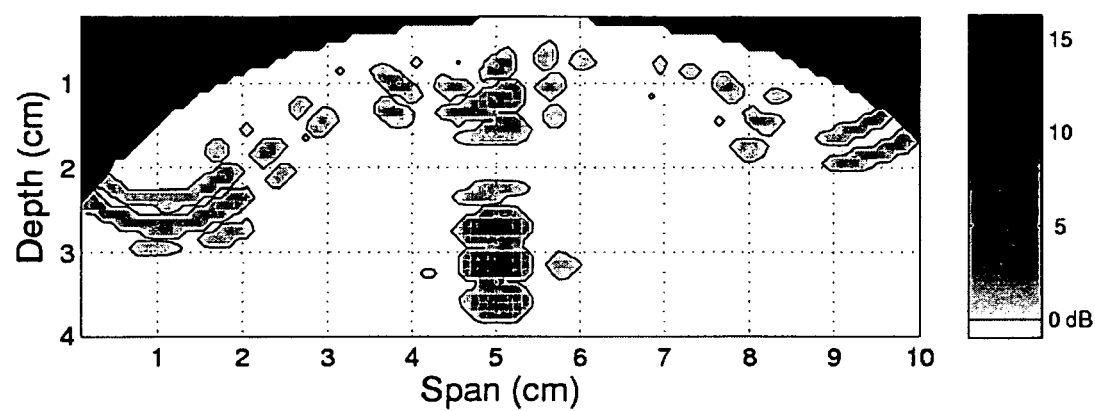
FIG. 8 illustrates an image of the thresholded test statistics in dB for the generalized likelihood ratio test (GLRT) with $P_{FA}=10^{-5}$ for backscatter from the model of FIG. 7 without clutter whitening.
Figure 9:
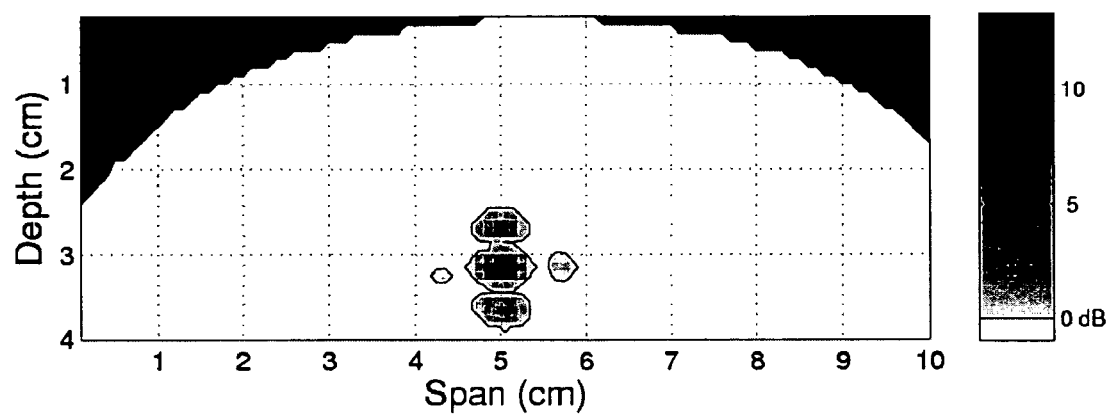
FIG. 9 illustrates an image of the thresholded test statistics for the GLRT with whitened backscatter from the numerical model of FIG. 7.
Figure 10:
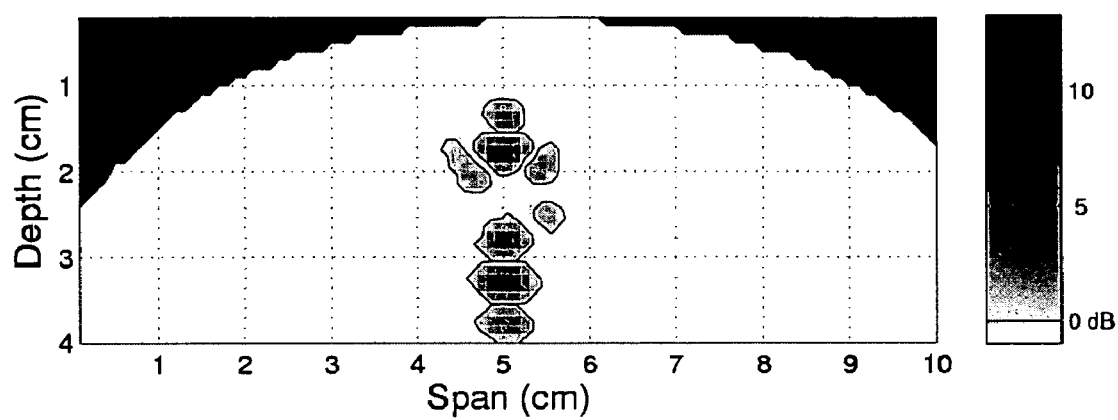
FIG. 10 illustrates an image of the thresholded test statistics for whitened backscatter from an FDTD model with two 2-mm diameter tumors that are vertically aligned.

Images of thresholded test statistics are plotted in FIGS. 8-10 for data generated using backscatter from a numerical breast model as discussed above plus additive white Gaussian noise. The noise power is set equal to the regularization parameter in the clutter whitening transformation. In FIGS. 8 and 9 the data contains backscatter generated from the FDTD model of FIG. 7. For FIG. 8 the GLRT is directly applied to the data without whitening the clutter, and for FIG. 9 the clutter model is used to whiten the data prior to applying the GLRT. The scale is measured in dB relative to the threshold value (0 dB) and grayscale values are assigned to each pixel in the displayed image in proportion to this scale.

Visual inspection of the images in FIGS. 8 and 9 indicates that the clutter whitening transformation effectively reduces the detectability of clutter. Furthermore, whitening has tightened the peak of the test statistic by reducing the correlation between neighboring signal vectors. The peak value of the test statistic significantly exceeds the threshold in both images and the location of the peak test statistic value coincides exactly with the center of the modeled tumor.

For the next example, the numerical breast model of FIG. 7 is modified to include a second 2-mm diameter tumor located 1.5 cm directly above the original tumor. Applying the same GLRT and plotting the thresholded test statistic produces the image in FIG. 10. Two distinct scatterers are apparent in the image and their peak values are within 1 dB of each other. In this case the peak values of the test statistic are each 1 mm away from the true tumor locations.

Additional simulations were performed on 2-D numerical breast phantoms to test the robustness of the GLRT and clutter whitening transformation. For a battery of simulations in which the tumor location, tumor size, tumor density, number of tumors, and normal tissue density were varied, the detector was effective in both detecting and localizing the modeled tumors.

Next we consider the GLRT applied to experimental backscatter waveforms from a 3-D physical breast phantom. The phantom consists of a homogeneous liquid that mimicks fatty normal breast tissue, and small synthetic tumors that exhibit approximately 3.3:1 dielectric-constant contrast with the fatty tissue simulant. We obtain experimental backscatter data for 7-by-7 planar antenna array positioned above a phantom containing a 4-mm-diameter, 4-mm-tall cylindrical scatterer located approximately 2 cm below the skin layer and centered under the antenna array. The GLRT is constructed from analytical signal templates for a 4-mm-diameter spherical tumor where the dielectric properties of the scatterer and surrounding medium match the corresponding dielectric properties of the physical phantom. Note that the scatterer shape in the physical phantom does not perfectly match the scatterer shape assumed in the GLRT templates. We allow this design mismatch because the cylindrical shape is most convenient for constructing the physical phantom and the spherical shape leads to a tractable analytical solution for the templates. We expect the impact of the mismatch to be minor since the dimensions of the cylinder and sphere are comparable and the tumor size is smaller than the wavelength at the center frequency of the UWB pulse. The templates are further parameterized by the position r, of the tumor which is scanned over the 6 cm×6 cm ×5 cm region of the breast phantom directly below the antenna array.

Figure 11:
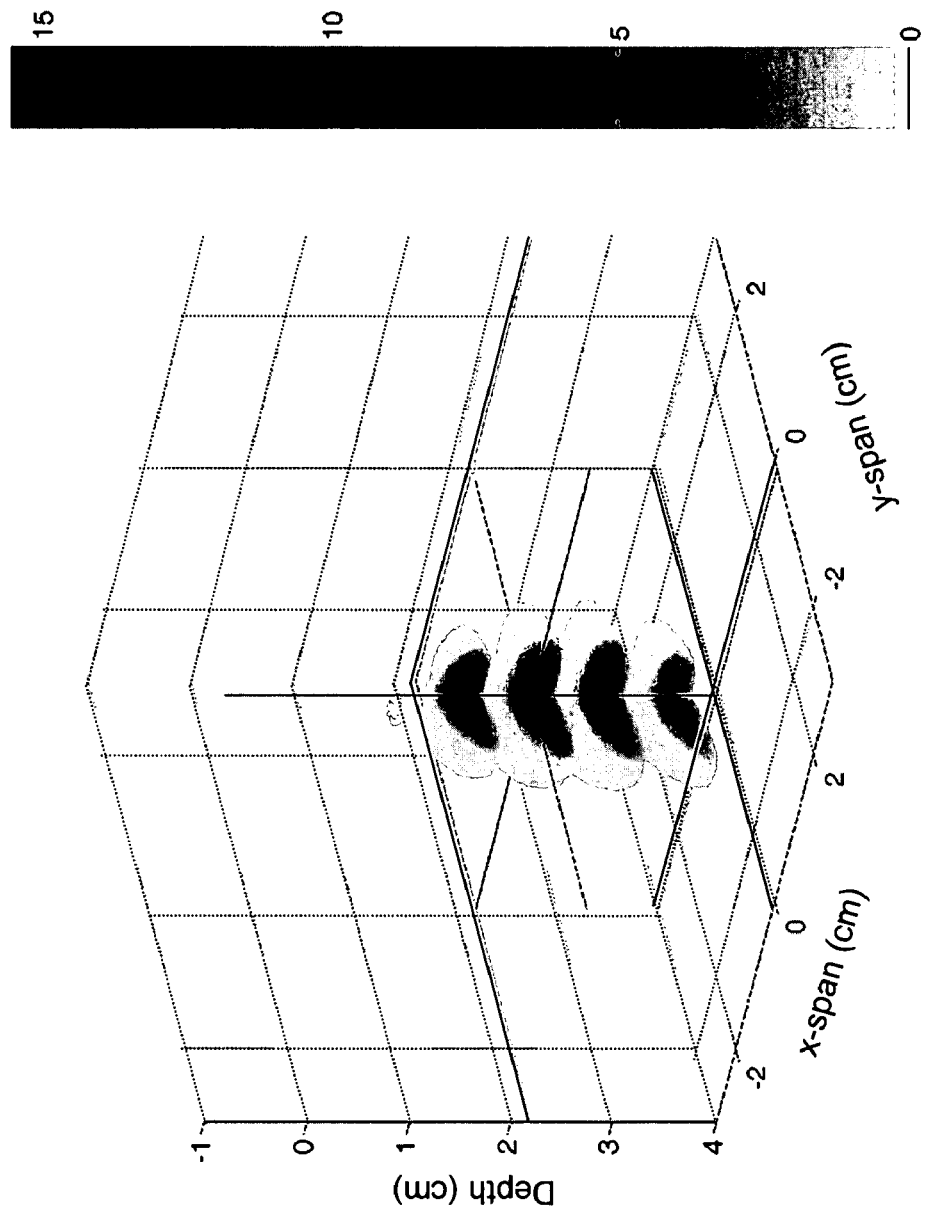
FIG. 11 illustrates a 3-D image of the thresholded test statistics for backscatter from a physical breast phantom with a single 4-mm diameter, 4-mm-tall cylindrical tumor approximately centered at (0 cm, 0 cm, 2 cm).

FIG. 11 depicts the resulting 3-D plot of the test statistic using the threshold value that enforces a FDR of $q^*=10^{-7}$. The peak test statistic occurs within 3 mm of the tumor in the phantom and the peak value is 14.7 dB above the threshold. Although the tumor is well-localized by the peak voxel in this image, multiple sidelobes above and below the true tumor location create some ambiguity in determining the number of scatterers detected. An iterative detection scheme may be utilized to overcome this ambiguity with only a linear increase in the number of computations. Note that the GLRT can be formulated to detect any number of scatterers simultaneously. However, testing for every possible combination of two or more scatterers in an image quickly becomes intractable for even a relatively small 2-D image. Instead, it is preferable to apply the GLRT iteratively, reformulating the test after each iteration to incorporate the known scatterer locations determined in previous iterations. The first iteration of the GLRT is performed as before. If any voxels in the image exceed the threshold, then the peak voxel $l_{max,1}$ is determined to be the location of a detected scatterer and the corresponding peak value is recorded. For the $(n+1)^{th}$ iteration of the GLRT with $n \geq 1$, we update the backscatter data model of eqn. (14) to reflect the n previously detected scatterers at known locations $l_{max,1}, \ldots l_{max,n}$;

$$y_i = a_{l_0} s_i(\theta_{l_0}) + \sum_{j=1}^{n} \alpha_{l_{max,j}} s_i(\theta_{l_{max,j}}) + c_i + n_i \qquad (20)$$

Whitening the data and signal vectors using the same transformation as before, we let $U(\theta_{l_{max,n}}) = [u(\theta_{l_{max,1}}) \ldots u(\theta_{l_{max,n}})]$ be a matrix whose columns are the whitened signal vectors corresponding to scatterers at the locations detected during the first n iterations. Then the updated GLRT test statistic for the $(n+1)^{th}$ iteration is given by $$t_{l,n+1} = c \frac{NM-n-1}{n+1} \frac{x^T P^\perp_{l_{max,n}} P_l P^\perp_{l_{max,n}} x}{x^T P^\perp_{l_{max,n}} (I - cP_l) P^\perp_{l_{max,n}} x} \qquad (21)$$

where $P_l$ is defined as before and $$c = \frac{u^T(\theta_l) u(\theta_l)}{u^T(\theta_l) P^\perp_{l_{max,n}} u(\theta_l)} \qquad (22)$$

$$P^\perp_{l_{max,n}} = I - U(\theta_{l_{max,n}}) [U^T(\theta_{l_{max,n}}) U(\theta_{l_{max,n}})]^{-1} U^T(\theta_{l_{max,n}}) \qquad (23)$$

The projection by $P_{l_{max,n}}^\perp$ onto the space orthogonal to the columns of $U(\theta_{l_{max,n}})$ eliminates the portion of the data that is correlated with previously detected scatterers in the current iteration of the test. This results in the "removal" of the previously detected scatterers and their sidelobes from the image generated during the $(n+1)^{th}$ iteration.

Figure 12:
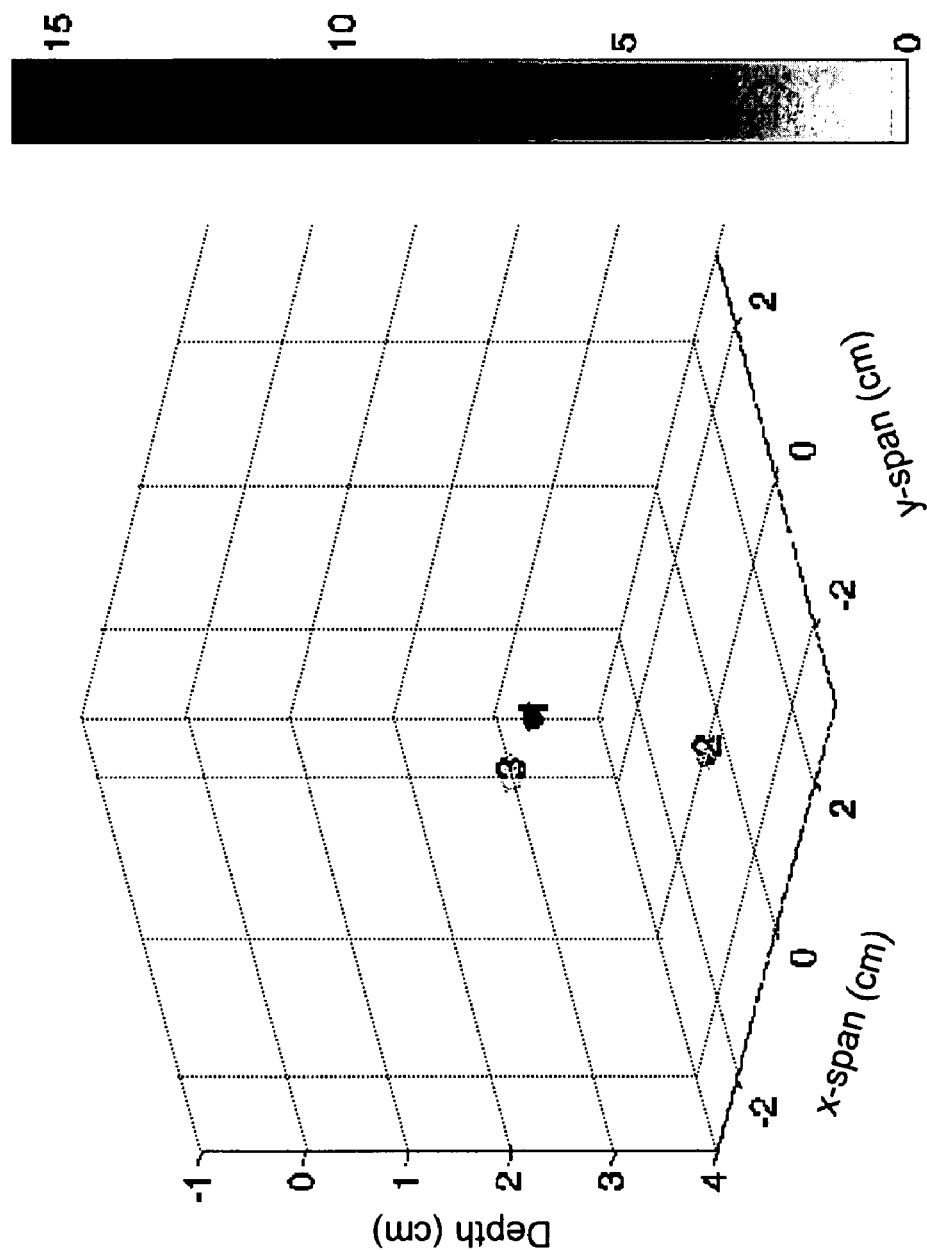
FIG. 12 shows a summary of detected scatterers for the single-tumor physical breast phantom using an iterative application of the GLRT. The dots numbered 1 through 3 represent the peak test statistic values and locations for iterations 1 through 3, respectively.

An image resulting from this iterative application of the GLRT to backscatter data from the physical phantom described above is depicted in FIG. 12. Each of the numbered dots in the image denotes the peak location and value for the labeled iteration of the GLRT. For three iterations, scatterers were detected. The first iteration correctly detected and localized the tumor in the breast phantom. The second two iterations falsely detected scatterers but at significantly reduced values of the test statistic. These false detections were likely due to several sources of mismatch between the GLRT signal templates and the true experimental backscattered signal from the tumor in the physical phantom. Sources of mismatch in this scenario include remnants from the artifact removal algorithm, distortion of the radiating pulse by the UWB antenna (which is unaccounted for by the GLRT templates), and the minor mismatch in the tumor shape. When the physical breast phantom contains multiple tumors as in this next example, the iterative GLRT is effective for isolating the effects of each tumor since the main and sidelobes associated with each tumor are removed one at a time. For a physical phantom containing two similar 4-mm-diameter, 4-mm-tall tumors at a depth of 2 cm and separated on the x-axis by approximately 1.8 cm, a single iteration of the GLRT yields the image shown in FIG. 13. After applying further iterations of the GLRT to the backscatter data, the summary of detected scatterers is shown in FIG. 14. The first two iterations correctly detect the two tumors and localize them to within a few mm. The test statistic values are 10.3 dB and 8.9 dB above the threshold for the first and second iterations respectively. A third iteration also produced a peak test statistic value above the threshold although there is no third tumor in the phantom. However, the peak value for this iteration is only 1.9 dB above the threshold and this erroneous detection can probably be attributed to the many sources of mismatch that occur between the ideal signal templates and the experimental signal backscatter.

The following considers the loss in GLRT power as mismatch is systematically introduced. The discussion primarily focuses on mismatch in the location parameter ($l \neq l_0$), but the results are valid for any type of model mismatch since the effect of mismatch is a function of the angle between the assumed and actual signal vectors. The relationship between mismatch angle and two example signal parameters, tumor size and tumor location, is empirically investigated. It is assumed for simplicity that the data is composed of a multichannel signal vector plus white Gaussian noise with variance $\sigma^2$.

Under matched conditions, the test statistic $t_l$ from eqn. (17) is distributed as noncentral F with noncentrality parameter, $$\delta_{l_0} = \frac{\alpha_{l_0}^2}{\sigma^2} u^T(\theta_{l_0}) u(\theta_{l_0}).$$

Note that the noncentrality parameter specifies the signal-to-noise ratio (SNR) of the data. When mismatch occurs ($l \neq l_0$) the distribution of the test statistic is doubly noncentral F with noncentrality parameters $\delta_l$, and $\delta_l^\perp$:

$$\delta_l = \frac{\alpha_{l_0}^2}{\sigma^2} \frac{|u^T(\theta_l) u(\theta_{l_0})|^2}{|u^T(\theta_l) u(\theta_l)|} = \delta_{l_0} \cos^2 \phi \quad (24)$$

$$\delta_l^\perp = u^T(\theta_l) P_l^\perp u(\theta_{l_0}) = \delta_{l_0} \sin^2 \phi \quad (25)$$

Here $$\cos^2 \phi = \frac{|u^T(\theta_l) u(\theta_{l_0})|^2}{|u^T(\theta_l) u(\theta_l)||u^T(\theta_{l_0}) u(\theta_{l_0})|}$$

so $\phi$ is the geometric angle between the assumed and actual signal vectors $u(\theta_l)$ and $u(\theta_{l_0})$, respectively. Note that mismatch decreases the noncentrality parameter in the numerator and increases the denominator noncentrality parameter. Consequently, the probability of detection $P_D$ decreases as $\phi$ increases on $$\left[0, \frac{\pi}{2}\right].$$

We evaluate mismatch loss on a logarithmic scale based on the decrease in numerator noncentrality parameter, $-10 \log (\cos^2 \phi)$.

The curves in FIG. 15 illustrate the relationship between $P_D$ and SNR ($\delta_{l_0}$) for the matched GLRT and for several mismatched GLRTs. Mismatch loss causes the curves to shift right. Thus, for a fixed $P_D$, introducing a nonzero mismatch loss effectively reduces the SNR of the data.

The following examines the configuration-specific relationship between mismatch loss and signal parameters. First, assuming that tumor location is the only signal parameter, the mismatch loss is calculated as the offset between the true and assumed tumor locations is varied. FIG. 16 displays two curves that represent horizontal (span axis) and vertical (depth axis) offsets in location. These calculations use the signal templates described above, whitened by the clutter model. The template location parameter $r_l$ is set to the test cell at (5.0, 2.1) cm and the true tumor location $r_{l_0}$ is varied about $r_l$. Since the antenna array and breast model are nearly symmetric about $r_l$ in the span (horizontal) axis, the mismatch loss due to horizontal error is also nearly symmetric. However, the mismatch loss due to depth (vertical) error is asymmetric with greater loss associated with the deeper locations. The local minima in the mismatch loss approximately 5 mm from the true location may result in false detections, especially at high SNR, and the presence of these sidelobes are evident in the examples of FIGS. 7-10. These results also suggest that a 1 mm sampling interval is sufficient for tumor detection since the mismatch loss is negligible when the test location is within 0.5 mm of the true location.

Next, a second parameter is introduced into the signal templates, namely tumor diameter. FIG. 17 depicts the mismatch loss when both tumor diameter and tumor location (in the depth axis) are mismatched. The figure illustrates that a mismatch in tumor size will introduce a localization error in the depth axis. That is, the peak of the test statistic occurs at the incorrect depth, but the tumor will still be detected if the SNR is high enough.

While the present invention may be utilized by itself for initial detection of potentially cancerous tumors, it may also be used in conjunction with other detection techniques to further confirm the presence of a tumor or to determine characteristics of a detected tumor, such as size, shape, and density. In particular, the present invention may be used in conjunction with microwave imaging via space-time beamforming as discussed in X. Li, et al., August, 2004, supra, and published U.S. patent application 2003/0088180A1.

It is understood that the invention is not limited to the embodiments set forth herein for purposes of illustrating the invention, but embraces all such forms thereof as come within the scope of the following claims.

What is claimed is:

1. A microwave system for examining an object comprising:

(a) an array of antennas for radiating and receiving microwaves;

(b) a microwave source connected to the array of antennas to provide microwave signals of a selected bandwidth to the antennas;

(c) a receiver connected to the antennas to detect the microwave signals received by the antennas and provide signal data corresponding thereto; and (d) a computer connected to receive the signal data, the computer programmed to process the signal data to fowl a space-time vector of signal data from each antenna for a candidate location, to determine a test statistic for the candidate location as the ratio of the sample variances under the two hypotheses of scatterer or no scatterer at the candidate location, to compare the test statistic with a selected threshold and assign a null hypothesis value to the selected location if the test statistic is below the threshold and to assign the test statistic value to the candidate location if the statistic is above the threshold, and to repeat the process for a plurality of different candidate locations in the object to be examined to generate multi-dimensional output data.

2. The system of claim 1 including an output device connected to the computer to display the multi-dimensional output data as a function of candidate locations.

3. The system of claim 1 wherein the computer is further programmed to determine the test statistic $t^l$ for time series data of length N for M channels as $$t_l = (NM - 1)\frac{x^T P_l x}{x^T P_l^\perp x}$$

where x is the multichannel data, $u(\theta_l)$ is the multichannel signal vector, and $P_l = u(\theta_l)[u^T(\theta_l)u(\theta_l)]^{-1}u^T(\theta_l)$ and $P_l^\perp = I_{NM} - P_l$ are orthogonal projection matrices.

4. The system of claim 3 wherein the null hypothesis value is zero.

5. The system of claim 1 wherein the microwave source provides pulses having pulse widths on the order of 100 picoseconds or less in duration.

6. The system of claim 1 wherein the microwave source is connected to the antennas to provide signals to one antenna at a time.

7. The system of claim 1 wherein the microwave source is connected to the antennas to provide signals to all of the antennas simultaneously.

8. The system of claim 1 wherein the threshold value provides a selected false detection rate by rejecting the null hypotheses.

9. The system of claim 1 further including signal processing circuitry that receives pulses from the microwave source and passes the pulses through a delay and a filter for each antenna before providing the delayed and filtered pulses to the antennas, the delays and filters selected to focus the radiated microwave energy from the array of antennas at a selected candidate location in the object.

10. The system of claim 1 wherein the computer is programmed to carry out clutter whitening on the corrected data.

11. The system of claim 1 wherein the computer programmed to estimate an artifact reflection component of the signal at each antenna as a filtered combination of the signals at all other antennas and to subtract the estimated artifact reflection component from the signal data to provide corrected signal data, with weights of the filters chosen to minimize the residual signal over that portion of the received data dominated by the reflection.

12. A method of carrying out microwave examination of an individual comprising:

(a) transmitting microwave signals from a plurality of antenna locations into an individual to be examined;

(b) receiving backscattered microwave signals at a plurality of antenna locations to provide received signals from the plurality of antenna locations;

(c) processing the received signals in a computer to form a space-time vector of signal data from each antenna for a candidate location, determining a test statistic for the candidate location as the ratio of the sample variances under the two hypotheses of scatterer or no scatterer at the candidate location, comparing the test statistic with a selected threshold and assigning a null hypothesis value to the candidate location if the test statistic is below the threshold and assigning the test statistic value to the candidate location if the statistic is above the threshold; and (d) then scanning the process to a plurality of different candidate locations in the individual and repeating steps (a), (b) and (c) at each candidate location to generate multi-dimensional output data.

13. The method of claim 12 wherein the step of transmitting microwave signals comprises transmitting microwave pulses having pulse widths on the order of 100 picoseconds or less in duration.

14. The method of claim 12 wherein the step of transmitting microwave signals comprises transmitting microwave pulses having frequency content at 10 GHz or higher.

15. The method of claim 12 including transmitting the microwave signals from an array of antennas so as to focus the microwave power on a candidate location.

16. The method of claim 12 further including, before the step of processing the received signals, the step of:

carrying out an artifact response subtraction process on the received signals in the computer by estimating the interface reflection component of the signal at each antenna location as a combination of the received signals at the other antenna locations passed through filters to provide corrected signal data, the filters having weights chosen to minimize the received signal over that portion of the received signal dominated by the artifact response, and providing the corrected signal data to the beamformer process.

17. The method of claim 12 wherein microwave signals are provided to one antenna at a time and backscattered microwave signals are received from one antenna at a tune for each of the antenna locations.

18. The method of claim 12 wherein microwave signals are transmitted from all of the antennas simultaneously and backscattered microwave signals are received from all of the antennas simultaneously.

19. The method of claim 12 wherein the step of transmitting the microwave signals is carried out simultaneously from all of the antenna locations by passing microwave pulses for each antenna at an antenna location through a delay and a filter for each antenna, the delays and filters selected to focus the radiated microwave energy from the antennas at a selected candidate location in the object.

20. The method of claim 12 wherein the computer is further programmed to determine the test statistic $t_l$ for time series data of length N for M channels as $$t_l = (NM - 1)\frac{x^T P_l x}{x^T P_l^\perp x}$$

where x is the multichannel data, $u(\theta_l)$ is the multichannel signal vector, and $P_l = u(\theta_l)[u^T(\theta_l)u(\theta_l)]^{-1}u^T(\theta_l)$ and $P_l^\perp = I_{NM} - P_l$ are orthogonal projection matrices.

21. The method of claim 12 wherein the null hypothesis value is zero.

22. The method of claim 12 further including the step of carrying out clutter whitening on the signal data.

23. A microwave system for examining an object comprising:
(a) an array of antennas for radiating and receiving microwaves;
(b) a microwave source connected to the array of antennas to provide microwave signals of a selected bandwidth to the antennas;
(c) a receiver connected to the antennas to detect the microwave signals received by the antennas and provide signal data corresponding thereto; and
(d) a computer connected to receive the signal data, the computer programmed to process the signal data to form a space-time vector of signal data from each antenna for a candidate location, to determine a generalized likelihood ratio test (GLRT) statistic for the candidate location as the ratio of the sample variances under the two hypotheses of a scatterer having a selected characteristic or no scatterer having the selected characteristics at the candidate location and to repeat the process for a plurality of different candidate locations in the object to be examined to generate multi-dimensional output data.

24. The system of claim 23 wherein the computer is programmed to compare the GLRT test statistic with a selected threshold and assign a null hypothesis value to the selected location if the test statistic is below the threshold and to assign the test statistic value to the candidate location if the statistic is above the threshold.

25. The system of claim 24 including an output device connected to the computer to display the multi-dimensional output data as a function of candidate locations.

26. The system of claim 23 wherein the computer is programmed to determine the GLRT test statistic $t_l$ for time series data of length N for M channels as $$t_l = (NM-1)\frac{x^T P_l x}{x^T P_l^\perp x}$$

where x is the multichannel data, $u(\theta_l)$ is the multichannel signal vector, and $P_l = u(\theta_l)[u^T(\theta_l)u(\theta_l)]^{-1}u^T(\theta_l)$ and $P_l^\perp = I_{NM} - P_l$ are orthogonal projection matrices.

27. The system of claim 23 wherein the microwave source provides pulses having pulse widths on the order of 100 picoseconds or less in duration.

28. The system of claim 23 wherein the microwave source is connected to the antennas to provide signals to one antenna at a time.

29. The system of claim 23 wherein the microwave source is connected to the antennas to provide signals to all of the antennas simultaneously.

30. The system of claim 23 wherein computer programmed to estimate an artifact reflection component of the signal at each antenna as a filtered combination of the signals at all other antennas and to subtract the estimated artifact reflection component from the signal data to provide corrected signal data, with weights of the filters chosen to minimize the residual signal over that portion of the received data dominated by the reflection.

31. The system of claim 23 wherein the computer is programmed to determine if there are more than one target scatterer locations and to carry out one or more iterations of the GLRT test using the scatterer locations determined in a prior iteration of the GLRT test.

32. The system of claim 23 wherein the computer is programmed to carry out clutter whitening on the corrected data.

33. A method of carrying out microwave examination of an individual comprising:
(a) transmitting microwave signals from a plurality of antenna locations into an individual to be examined;
(b) receiving backscattered microwave signals at a plurality of antenna locations to provide received signals from the plurality of antenna locations;
(c) processing the received signals in a computer to form a space-time vector of signal data from each antenna for a candidate location, determining a generalized likelihood ratio test (GLRT) statistic for the candidate location as the ratio of the sample variances under the two hypotheses of scatterer having a selected characteristic or no scatterer having the selected characteristic at the candidate location; and
(d) then scanning the process to a plurality of different candidate locations in the individual and repeating steps (a), (b) and (c) at each candidate location to generate multi-dimensional output data.

34. The method of claim 33 further comprising comparing the GLRT test statistic with a selected threshold and assigning a null hypothesis value to the candidate location if the test statistic is below the threshold and assigning the test statistic value to the candidate location if the statistic is above the threshold.

35. The method of claim 33 wherein the step of transmitting microwave signals comprises transmitting microwave pulses having pulse widths on the order of 100 picoseconds or less in duration.

36. The method of claim 33 wherein the step of transmitting microwave signals comprises transmitting microwave pulses having frequency content at 10 GHz or higher.

37. The method of claim 33 further including, before the step of processing the received signals, the step of:
carrying out an artifact response subtraction process on the received signals in the computer by estimating the interface reflection component of the signal at each antenna location as a combination of the received signals at the other antenna locations passed through filters to provide corrected signal data, the filters having weights chosen to minimize the received signal over that portion of the received signal dominated by the artifact response, and providing the corrected signal data to the beamformer process.

38. The method of claim 33 wherein the computer is programmed to determine the GLRT test statistic $t_l$ for time series data of length N for M channels as $$t_l = (NM-1)\frac{x^T P_l x}{x^T P_l^\perp x}$$

where x is the multichannel data, $u(\theta_l)$ is the multichannel signal vector, and $P_l = u(\theta_l)[u^T(\theta_l)u(\theta_l)]^{-1}u^T(\theta_l)$ and $P_l^\perp = I_{NM} - P_l$ are orthogonal projection matrices.

39. The method of claim 33 wherein the null hypothesis value is zero.

40. The method of claim 33 further including the step of carrying out clutter whitening on the signal data.

41. The method of claim 33 wherein if more than one target scatterer location is found, steps (a)-(d) are carried out in one or more iterations using the scatterer locations determined in a prior iteration.

* * * * *

UNITED STATES PATENT AND TRADEMARK OFFICE
CERTIFICATE OF CORRECTION

PATENT NO. : 8,050,740 B2
APPLICATION NO. : 10/942115
DATED : November 1, 2011
INVENTOR(S) : Shakti K. Davis It is certified that error appears in the above-identified patent and that said Letters Patent is hereby corrected as shown below:

IN THE SPECIFICATION:

Col. 3, line 20
Delete "signal ocs" and replace with -- signal $\alpha$s --

Col. 9, line 29
Delete "$\epsilon_r$," and replace with -- $\varepsilon_r$ --

Col. 14, line 15
Delete "$n_l$" and replace with -- $n_i$ --

Col. 16, line 8
Delete "parameter A" and replace with -- parameter $\lambda$ --

Col. 17, line 55
Delete "position r" and replace with -- position $r_l$ --

Col. 18, line 33
Delete "where P" and replace with -- where $P_l$ --

IN THE CLAIMS

Col. 20, line 65 (Claim 1)
Delete "fowl" and replace with -- form --

Col. 21, line 15 (Claim 3)
Delete "$t^l$" and replace with -- $t_l$ --

Signed and Sealed this
Twenty-fourth Day of January, 2012

David J. Kappos
*Director of the United States Patent and Trademark Office*

CERTIFICATE OF CORRECTION (continued)
U.S. Pat. No. 8,050,740 B2

Col. 22, line 38 (Claim 17)
Delete "tune" and replace with -- time --

Col. 22, line 62 (Claim 20)
Delete "orthogonalprojection" and replace with -- orthogonal projection --